United States Patent
Cheng et al.

(10) Patent No.: US 11,900,703 B2
(45) Date of Patent: Feb. 13, 2024

(54) SYSTEMS AND METHODS FOR AUTOMATED TAGGING OF DIGITAL HISTOLOGY SLIDES

(71) Applicant: HistoWiz, Inc., Brooklyn, NY (US)

(72) Inventors: Ke Cheng, Brooklyn, NY (US); Matthew Wilder, Boulder, CO (US); Weijian Li, Rochester, NY (US)

(73) Assignee: HistoWiz, Inc., Brooklyn, NY (US)

( * ) Notice: Subject to any disclaimer, the term of this patent is extended or adjusted under 35 U.S.C. 154(b) by 0 days.

(21) Appl. No.: 18/229,585

(22) Filed: Aug. 2, 2023

(65) Prior Publication Data

US 2023/0377353 A1    Nov. 23, 2023

Related U.S. Application Data

(63) Continuation of application No. PCT/US2022/039936, filed on Aug. 10, 2022.

(60) Provisional application No. 63/232,039, filed on Aug. 11, 2021.

(51) Int. Cl.
| | |
|---|---|
| *G06K 9/00* | (2022.01) |
| *G06V 20/69* | (2022.01) |
| *G06V 10/77* | (2022.01) |
| *G06V 10/70* | (2022.01) |
| *G06V 10/82* | (2022.01) |
| *G06V 20/70* | (2022.01) |
| *G06F 16/532* | (2019.01) |

(52) U.S. Cl.
CPC .......... *G06V 20/698* (2022.01); *G06F 16/532* (2019.01); *G06V 10/70* (2022.01); *G06V 10/7715* (2022.01); *G06V 10/82* (2022.01); *G06V 20/695* (2022.01); *G06V 20/70* (2022.01); *G06V 2201/03* (2022.01)

(58) Field of Classification Search
None
See application file for complete search history.

(56) References Cited

U.S. PATENT DOCUMENTS

| | | | |
|---|---|---|---|
| 2016/0042511 A1 | 2/2016 | Chukka et al. | |
| 2019/0355113 A1* | 11/2019 | Wirch | G16H 50/70 |
| 2020/0205790 A1 | 7/2020 | Dewan et al. | |
| 2020/0342597 A1 | 10/2020 | Chukka et al. | |
| 2021/0056287 A1 | 2/2021 | Schaumburg et al. | |

(Continued)

FOREIGN PATENT DOCUMENTS

| | | |
|---|---|---|
| CN | 112149619 A | 12/2020 |
| WO | WO-2023014968 A1 | 2/2023 |
| WO | WO-2023018785 A2 | 2/2023 |

OTHER PUBLICATIONS

Lu et al., "Data efficient and weakly supervised computational pathology on whole slide images", (Year: 2020).*

(Continued)

*Primary Examiner* — Soo Jin Park
(74) *Attorney, Agent, or Firm* — Wilson Sonsini Goodrich & Rosati

(57) ABSTRACT

Provided herein are methods and systems for performing an automated tagging of features in digital micrographs representing slides with tissue samples. Automated tagging of features may include automated entry of metadata associated with whole slide images or regions of the whole slide images.

26 Claims, 8 Drawing Sheets
(1 of 8 Drawing Sheet(s) Filed in Color)

(56) References Cited

U.S. PATENT DOCUMENTS

2021/0090238 A1 3/2021 Gallagher-Gruber et al.
2021/0295111 A1 9/2021 Campanella et al.

OTHER PUBLICATIONS

Hashimoto et al., "Multi-scale domain-adversarial multiple-instance CNN for cancer subtype classification with unannotated histopathological images" (Year: 2020).*
PCT/US2022/039568 International Search Report and Written Opinion dated Nov. 1, 2022.
PCT/US2022/039936 International Search Report and Written Opinion dated Feb. 14, 2023.

* cited by examiner

SYSTEMS AND METHODS FOR AUTOMATED TAGGING OF DIGITAL HISTOLOGY SLIDES

CROSS-REFERENCE

This application is a continuation of PCT/US22/39936 filed Aug. 10, 2022 which claims the benefit of U.S. Provisional Application No. 63/232,039 filed on Aug. 11, 2021, which application is incorporated herein by reference in its entirety.

BACKGROUND

Histopathology is the microscopic examination of tissue in order to study the manifestations of disease. Typically, histology slides are examined by a pathologist to interpret the histology slides and provide a pathology report describing findings and the opinion of the pathologist. Computer systems may provide methods of automating the interpretation of histology slides and classification of whole slide images or of various regions of the histology slides.

SUMMARY

In some embodiments, provided herein is a method of automatic multi-tagging of whole slide histopathology images comprising: receiving a digital whole slide image; sampling a plurality of non-background patches from the whole slide image at a plurality of magnifications; applying a machine learning model to predict multiple slide-level tags from the plurality of non-background patches, wherein the machine learning model comprises: a first module configured to extract a visual feature representation of each patch; a second module configured to modulate patch features by providing the extracted visual feature representations as inputs to a first attention aggregation mechanism performing operations comprising: mapping each visual feature representation into different attention-weighted features through multi-head attentions and outputting a weighted patch feature comprising an aggregation of the visual feature representations and the attention-weighted features; wherein the machine learning model operates in a multi-scale mode utilizing the patches at the plurality of magnifications to identify both patch features and magnification levels most discriminant for the multi-tagging; a third module configured to construct slide-level tags identifying tag classifications by providing the weighted patch features to a plurality of second attention aggregation mechanisms, one per output head, each performing operations comprising: mapping each weighted patch feature into different attention-weighted features through multi-head attentions, and outputting a slide-level tag comprising an aggregation of the attention-weighted features; and associating the multiple slide-level tags with the digital whole slide image.

In some embodiments, the method further comprises detecting regions of the slide comprising tissue, detecting regions of the slide comprising background, or both. In some embodiments, the first module utilizes a neural network. In some embodiments, the neural network is a deep neural network. In some embodiments, the deep neural network comprises a ResNet architecture. In some embodiments, the ResNet architecture comprises ResNet-34, ResNet-50, or ResNet-101. In some embodiments, the second module utilizes a neural network. In some embodiments, the neural network utilized by the second module is a deep neural network.

In some embodiments, the first attention aggregation mechanism further performs operations comprising: adding a residual connection from each input to the output and directly aggregating it with each patch's weighted representations. In some embodiments, the plurality of magnifications includes magnifications from about 4× to about 100×. In some embodiments, the plurality of magnifications comprises about 3 magnifications to about 10 magnifications.

In some embodiments, the tags are selected from the group consisting of: species, age, gender, organ type, stain type, lesion type, cell type, disease type, antibodies, fixative type, gene expression, tumor type, biosystem, mouse strain, genetically engineered mouse model (GEMM), experiment, xenograft, promoter, reporter, and combinations thereof. In some embodiments, lesion type comprises one or more of: tumor, necrosis, fibrosis, and metastasis.

In some embodiments, one or more of the tags are Boolean. In some embodiments, one or more of the tags comprise a string defining a type. In some embodiments, one or more of the tags comprise a string or number defining a severity. In some embodiments, one or more of the tags comprise a string or coordinate representation defining a location. In some embodiments, each tag is associated with the digital whole slide image as a metadata field.

In some embodiments, the method further comprises archiving the digital whole slide image and the associated tags in database. In some embodiments, the method further comprises providing a slide image search interface providing access to configure a slide image search module. In some embodiments, the slide image search interface allows a user to perform a reverse image search. In some embodiments, the slide image search interface allows a user to identify archived whole slide images by matching one or more tag attributes. In some embodiments, the slide image search interface allows a user to identify archived whole slide images by thresholding one or more tag attributes. In some embodiments, the machine learning model is trained under a multi-task learning scheme where each classification task is a multi-class classification problem.

In some embodiments, provided herein is a system comprising: at least one processor, a memory, and instructions executable by the at least one processor to create a whole slide histopathology image multi-tagging application comprising: a software module configured to receive a digital whole slide image and sample a plurality of non-background patches from the whole slide image at a plurality of magnifications; a machine learning model to predict multiple slide-level tags from the plurality of non-background patches, wherein the machine learning model comprises: a visual feature extraction module configured to extract a visual feature representation of each patch; a patch transformation module configured to modulate patch features by providing the extracted visual feature representations as inputs to a first attention aggregation mechanism performing operations comprising: mapping each visual feature representation into different attention-weighted features through multi-head attentions and outputting a weighted patch feature comprising an aggregation of the visual feature representations and the attention-weighted features; wherein the machine learning model operates in a multi-scale mode utilizing the patches at the plurality of magnifications to identify both patch features and magnification levels most discriminant for the multi-tagging; a multi-tag attention module configured to construct slide-level tags identifying tag classifications by providing the weighted patch features to a plurality of second attention aggregation mechanisms, one per output head, each performing operations comprising: mapping each weighted patch feature into different attention-weighted features through multi-head attentions, and outputting a slide-level tag comprising an aggregation of the attention-weighted features; and a software module configured to associate the multiple slide-level tags with the digital whole slide image.

In some embodiments, provided herein is a non-transitory computer-readable storage media encoded with a computer program including instructions executable by a processor to create a whole slide histopathology image multi-tagging application comprising: an intake module configured to receive a digital whole slide image and sample a plurality of non-background patches from the whole slide image at a plurality of magnifications; a machine learning model to predict multiple slide-level tags from the plurality of non-background patches, wherein the machine learning model comprises: a visual feature extraction module configured to extract a visual feature representation of each patch; a patch transformation module configured to modulate patch features by providing the extracted visual feature representations as inputs to a first attention aggregation mechanism performing operations comprising: mapping each visual feature representation into different attention-weighted features through multi-head attentions and outputting a weighted patch feature comprising an aggregation of the visual feature representations and the attention-weighted features; wherein the machine learning model operates in a multi-scale mode utilizing the patches at the plurality of magnifications to identify both patch features and magnification levels most discriminant for the multi-tagging; a multi-tag attention module configured to construct slide-level tags identifying tag classifications by providing the weighted patch features to a plurality of second attention aggregation mechanisms, one per output head, each performing operations comprising: mapping each weighted patch feature into different attention-weighted features through multi-head attentions, and outputting a slide-level tag comprising an aggregation of the attention-weighted features; and a tagging module configured to associate the multiple slide-level tags with the digital whole slide image.

In some embodiments, provided herein is a method of automatic multi-tagging of histopathology images comprising: receiving a digital whole slide image or a portion thereof; sampling a plurality of non-background patches from the whole slide image or the portion thereof at a plurality of magnifications; applying a machine learning model to predict multiple tags from the plurality of non-background patches, wherein the machine learning model comprises: a first module configured to extract a visual feature representation of each patch; a second module configured to apply one or more neural networks using the visual feature representations of the patches as inputs to produce a heatmap demonstrating where multi-tagging attributes of interest are located within the whole slide image or the portion thereof; wherein the machine learning model operates in a multi-scale mode utilizing the patches at the plurality of magnifications to produce the heatmap; and a third module configured to construct tags identifying tag classifications and distributions based on the heatmap; and associating the multiple tags with the digital whole slide image or the portion thereof.

In some embodiments, the method further comprises detecting regions of the slide comprising tissue, detecting regions of the slide comprising background, or both. In some embodiments, the first module utilizes a neural network. In some embodiments, the neural network is a deep neural network. In some embodiments, the deep neural network comprises a ResNet architecture. In some embodiments, the ResNet architecture comprises ResNet-34, ResNet-50, or ResNet-101. In some embodiments, the second module utilizes a deep neural network. In some embodiments, the plurality of magnifications comprises magnifications from about 4× to about 100×. In some embodiments, the plurality of magnifications of magnifications comprises about 3 magnifications to about 10 magnifications. In some embodiments, the tags are selected from the group consisting of: species, age, gender, organ type, stain type, lesion type, cell type, disease type, antibodies, fixative type, gene expression, tumor type, biosystem, mouse strain, genetically engineered mouse model (GEMM), experiment, xenograft, promoter, reporter, and combinations thereof. In some embodiments, lesion type comprises one or more of: tumor, necrosis, fibrosis, and metastasis.

In some embodiments, one or more of the tags comprise a string or coordinate representation defining a location on the whole slide image or the portion thereof. In some embodiments, one or more of the tags are Boolean. In some embodiments, one or more of the tags comprise a string defining a type. In some embodiments, one or more of the tags comprise a string or number defining a severity. In some embodiments, one or more of the tags comprise a string or matrix defining a spatial density. In some embodiments, each tag is associated with the digital whole slide image or the portion thereof as a metadata field.

In some embodiments, the one or more neural networks comprise one or more fully convolutional neural networks. In some embodiments, the heatmap comprises a plurality of pixels, and wherein each is associated with a prediction between 0 and 1 that represents a probability of the attribute being present at the pixel location. In some embodiments, the heatmap comprises multiple dimensions, wherein each dimension corresponds to a different attributes being predicted, and wherein each pixel of the heatmap comprises a probability associated with each attribute.

In some embodiments, the third module is further configured to process the heatmap to extract coherent regions described by coordinates using a polygon, bounding box, or single point. In some embodiments, the multiple tags are associated with the polygon, bounding box, or single point. In some embodiments, the method further comprises archiving the digital whole slide image or the portion thereof and the associated tags in database. In some embodiments, the method further comprises providing a slide image search interface providing access to configure a slide image search module. In some embodiments, the slide image search interface allows a user to perform a reverse image search. In some embodiments, the slide image search interface allows a user to identify a reference portion of a slide and identify one or more other portions of the same slide or one or more portions of one or more different slides that are similar to the reference. In some embodiments, the slide image search interface allows a user to identify one or more portions of archived whole slide images by matching one or more tag attributes. In some embodiments, the slide image search interface allows a user to identify one or more portions of archived whole slide images by thresholding on one or more tag attributes. In some embodiments, the slide image search interface allows a user to perform a search based on the density of one or more tag representations in a heatmap. In some embodiments, the machine learning model is trained under a multi-task learning scheme where each classification task is a multi-class classification problem.

In some embodiments, provided herein is a system comprising: at least one processor, a memory, and instructions executable by the at least one processor to create a histopathology image multi-tagging application comprising: an intake module configured to receive a digital whole slide image or a portion thereof and sample a plurality of non-background patches from the whole slide image or the portion thereof at a plurality of magnifications; a machine learning model to predict multiple tags from the plurality of non-background patches, wherein the machine learning model comprises: a visual feature extraction module configured to extract a visual feature representation of each patch; a heatmapping module configured to apply one or more neural networks using the visual feature representations of the patches as inputs to produce a heatmap demonstrating where multi-tagging attributes of interest are located within the whole slide image or the portion thereof; wherein the machine learning model operates in a multi-scale mode utilizing the patches at the plurality of magnifications to produce the heatmap; and a multi-tag module configured to construct tags identifying tag classifications and distributions based on the heatmap; and a tagging module configured to associate the multiple tags with the digital whole slide image or the portion thereof.

In some embodiments, provided herein is a non-transitory computer-readable storage media encoded with a computer program including instructions executable by a processor to create a histopathology image multi-tagging application comprising: an intake module configured to receive a digital whole slide image or a portion thereof and sample a plurality of non-background patches from the whole slide image or the portion thereof at a plurality of magnifications; a machine learning model to predict multiple tags from the plurality of non-background patches, wherein the machine learning model comprises: a visual feature extraction module configured to extract a visual feature representation of each patch; a heatmapping module configured to apply one or more neural networks using the visual feature representations of the patches as inputs to produce a heatmap demonstrating where multi-tagging attributes of interest are located within the whole slide image or the portion thereof; wherein the machine learning model operates in a multi-scale mode utilizing the patches at the plurality of magnifications to produce the heatmap; and a multi-tag module configured to construct tags identifying tag classifications and distributions based on the heatmap; and a tagging module configured to associate the multiple tags with the digital whole slide image or the portion thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the subject matter described herein are set forth with particularity in the appended claims. A better understanding of the features and advantages of the present subject matter will be obtained by reference to the following detailed description that sets forth illustrative embodiments, in which the principles of the present subject matter are utilized, and the accompanying drawings of which:

DETAILED DESCRIPTION

Provided herein embodiments of systems and methods for processing tissue samples to form histology slides and analyzing said histology slides in an automated histopathological analysis. In some embodiments, systems and methods are provided herein for attributing metadata to whole slide images and image patch regions. The metadata may be utilized to search, sort, and categorize digital images of histology slides in a laboratory information management system (LIMS). In some embodiments, a patch based deep model Patch Transformer is designed for multi-tagging whole slide images. In some embodiments, the proposed model is trained end-to-end under a multi-task learning scheme where each task is a multi-class classification problem. In some embodiments, a Patch Transformation Module extracts patch characteristics considering global context with limited prior structural knowledge through a multi-head attention mechanism. In some embodiments, a Multi-Tag Attention Module constructs tag-specific representations by aggregating weighted patch features.

I. Workflow

A. Order Form

Figure 2:
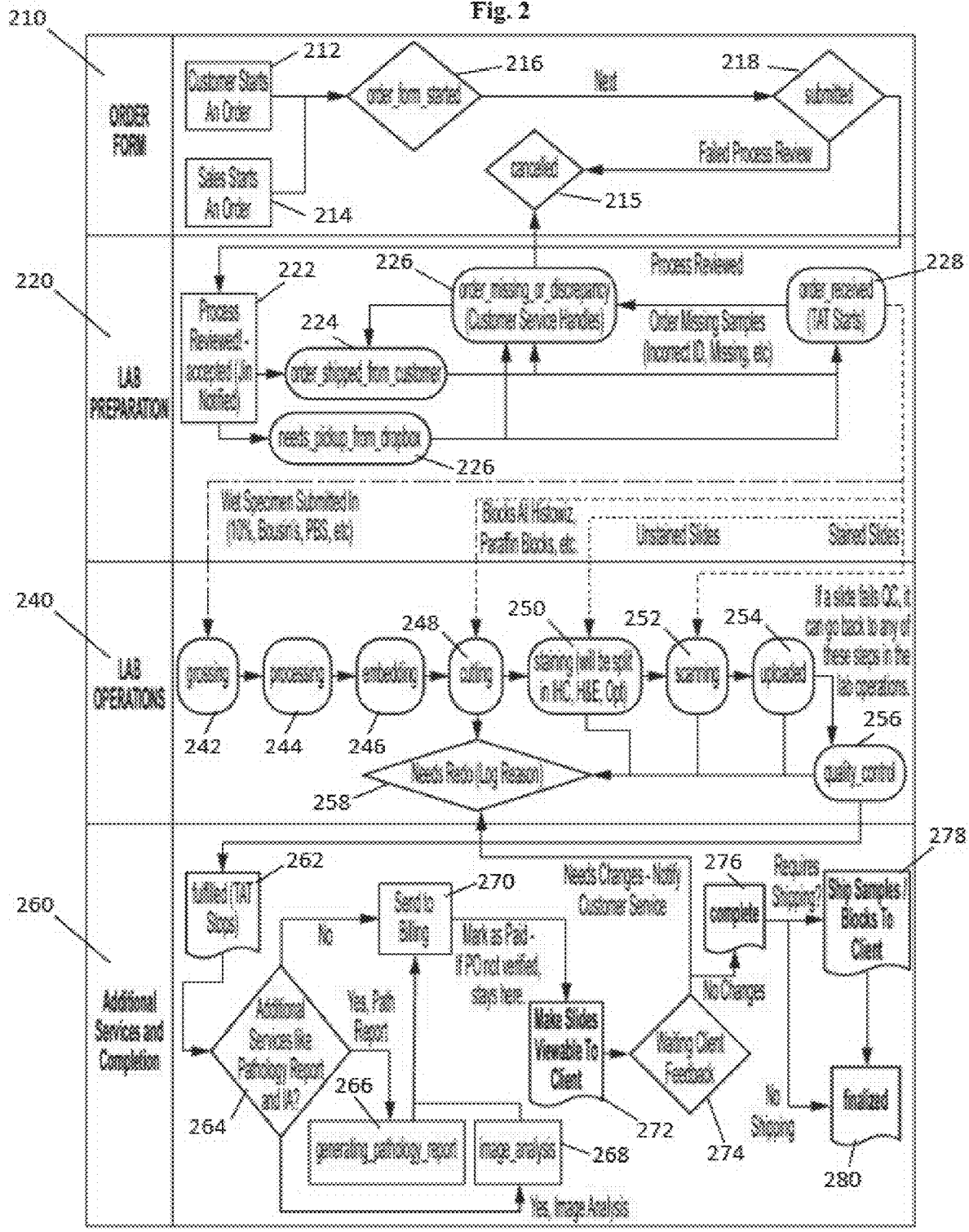
FIG. 2 depicts a non-limiting example of workflow of receiving and processing an order for analysis of a sample.

In some embodiments, the methods herein further comprise receiving and processing orders for a histopathological analysis. In some embodiments, methods herein comprise receiving tissue samples, processing the tissue samples to create histology slides, scanning the histology slides to create digital images of the histology slides, and processing the digital images of the histology slides to perform an automated histopathological analysis. With reference to FIG. 2, an embodiment of a workflow for processing and analysis of a tissue sample is depicted. In some embodiments, a histopathology analysis begins with initiation of an order from at step 210. In some embodiments, the order form comprises information about a subject, from which a tissue sample is provided from for a histopathological analysis. Subject information included on the order form may comprise a species of a subject, a location from which the tissue sample was obtained, a description of the region from which the tissue sample was obtained, an image of the region from which the tissue sample was obtained, an image of the region from which the tissue sample was obtained prior to a biopsy, an age of the subject, an image of the region from which the tissue sample was obtained after a biopsy, and symptoms and/or ailments of the subject to be further analyzed by the histological analysis.

In some embodiments, the subject is a human and the tissue sample is a human tissue sample. In some embodiments, the subject is an animal and the tissue sample is a veterinary tissue sample. In some embodiments, an order form comprises information such as a date of birth of a subject, a medical history of the subject, a description of symptoms experienced by the subject, the name of the subject, the residence of the subject, contact information for the subject, emergency contact information for the subject, and other information which is useful in identifying a subject or assessing a tissue sample. In some embodiments, human samples are processed for research purposes. In some embodiments, samples are deidentified prior to processing.

In some embodiments, at step 212, an order is initiated by a member of a sales team. In some embodiments, the sales team member is an employee of a laboratory for processing and analyzing histology slides. In some embodiments, the sales team member advocates for the lab or company to process the histology slides. In some embodiments, the sales team member receives the subject information and processes the information to fill out an order form. In some embodiments, at step 214, the order is initiated by a customer. A customer may include a physician, a researcher/scientist, a medical professional, or a legal professional submitting samples for an expert opinion.

In some embodiments, at step 216, an order form is started. In some embodiments, the order form is digital. The order form may be presented as a fillable form or web application. The order form may provide a graphical user interface to guide a customer or sales team member through input fields in order to obtain the information necessary to accurately process a sample and assign the sample to the subject.

In some embodiments, a sales team member assists a customer with filling out an order form. In some embodiments, a web application allows a sales team member to view and fill out the order form with the customer in real-time. In some embodiments, a sales team member communicates with the customer via an online chat during filling of an order form. In some embodiments, a sales team member communicates with the customer via phone during filling of an order form.

In some embodiments, the completed order form is then submitted, at step 218, to the laboratory which will be processing and analyzing the sample. In some embodiments, the submitted order form is then reviewed. During the review, a submitted order form may be analyzed to ensure all necessary information has been filled out. In some embodiments, information provided on the form is verified. In some embodiments, if the order form is missing critical information or appears to be incorrect then a representative will contact the client to resolve any discrepancies. In some embodiments, if it is determined that an order will be impossible to complete given the capabilities of the laboratory, then the order will be cancelled at step 215. In some embodiments, upon cancellation of an order the customer and/or sales team member will receive a notification. A cancellation notification may include reasons as to why the order has been cancelled.

In some embodiments, if the order form is correctly filled out then the order will be accepted at step 222. In some embodiments, an accepted order will be flagged for the laboratory team, such that they can expect to receive a sample or be notified of a location to pick up a sample to be processed and analyzed. In some embodiments, the laboratory provides a notification to a client. Notifications may be electronic notifications sent by email, text message, or other means. Notifications may include an alert that an order has been received and an alert that an order has been accepted. In some embodiments, a notification informing a client that the order has been accepted includes a shipping label for shipping the tissue sample.

B. Lab Preparation

In some embodiments, at step 220, preparation of a sample begins once an order has been accepted at step 222. In some embodiments, a client receives a notification that preparation of a sample has begun. If a sample is to be shipped to the laboratory, at step 224 then a notification may be received by the lab team, such that they can expect to receive the sample via shipping. In some embodiments, a member of the lab team picks up a sample from a drop box. The drop box may be provided within the lab, such that samples taken at the same facility may be placed in the drop box and picked up by a lab member for sampling.

At step 228, the order is received by the lab. In some embodiments, the order comprises one or more tissue samples. In some embodiments, the order comprises unstained histology slides. In some embodiments, the order comprises stained histology slides. In some embodiments, the order is checked to ensure the proper contents have been received. At step 226, if the order is missing samples or any discrepancies are present in the order then the order may be flagged. A flagged order may trigger a request for new samples to be shipped by the customer. In some embodiments, a flagged order will alert a sales representative who will reach out to the client to resolve any issues. In some embodiments, orders are marked as 'pending' until issues and/or discrepancies are resolved or a new sample is received. This may prevent improper identification of the orders and misdiagnosis.

C. Automated Histology/Lab Operations

In some embodiments, at step 240, the lab receives the sample and begins processing the sample. The sample may be received by the lab in one or more states of processing. In some embodiments, the sample is received by the lab is a wet sample, a fresh sample, a frozen sample, a fixed sample, a sample provided in neutral buffered formalin solution, sample provided in a Bouin solution, a sample provided in a phosphate buffered saline (PBS) solution, or a sample provided in another acceptable state or form. In some embodiments, the sample received by the lab is embedded. In some embodiments, the sample received by the lab has been sectioned into unstained glass slides. In some embodiments, the sample received by the lab has been sectioned into glass slides and stained.

In some embodiments, grossing begins at step 242, immediately after receiving the sample. During grossing, the sample may be inspected to identify improper sampling, preparation, handling, or imperfections prior to processing (e.g., in cassette molds) of the samples, which may affect the results of the analysis. In some embodiments, grossing includes taking measurements of the samples. In some embodiments, grossing includes determining how to cut a sample, such as bisecting or trisecting, where necessary to capture a region of interest or fit into a cassette mold for embedding. In some embodiments, a region of interest is specified in the instructions of an order, and the sample is cut accordingly to capture the region of interest. In some embodiments, grossing details are entered into the laboratory information system.

If a sample received by the lab has yet to be embedded, then the sample may undergo processing at step 244. Processing may comprise fixation of the sample. In some embodiments, processing of the sample may comprise dehydration to remove water from the sample. Dehydration may comprise immersing samples in a dehydrating solutions. In some embodiments, concentrations of dehydrating solutions are increased gradually to avoid distortion of the tissue sample. Dehydrating solutions may comprise acetone, butanol, Cellosolve, dimethoxypropane (DMP), diethoxypropane (DEP), dioxane, ethanol, methanol, isopropanol, polyethylene glycol, tetrahydrofuran, or other suitable dehydrating solutions.

In some embodiments, processing further comprises clearing of the dehydrating solution. In some embodiments, a clearing agent or intermediary fluid, which is miscible with an embedding media, replaces the dehydration solution. Exemplary clearing agents may include, but are not limited to xylene, toluene, chloroform, orange oil based solutions, and methyl salicylate, amyl acetate, methyl benzoate, methyl salicylate, benzene, butyl acetate, carbon tetrachloride, cedarwood oil, limonene, methyl benzoate, tepenes, trichloroethane, and other suitable clearing agents. In some embodiments, clearing the dehydrating solution is an automated process. Clearing may be accomplished in a span of about 1 hour to 24 hours, depending on the size of the tissue sample.

In some embodiments, the sample then undergoes embedding at step 246. In some embodiments, embedding comprises infiltrating the tissue sample with an embedding medium to provide a support to allow the tissue sample to be cut or sectioned into thin slices to be provided on a slide. In some embodiments, an embedding medium comprises paraffin wax, ester wax, plasticizers, epoxy resin, acrylic resin, acrylic agar, gelatin, celloidin, water-soluble wax, other types of waxes, or other suitable embedding material mediums. In some embodiments, frozen samples are placed in a water-based embedding medium such as water-based glycol, an optimal cutting temperature (OCT) compound, tris-buffered saline (TBS), Cryogel, or resin. In some embodiments, the embedding medium and the tissue samples are placed in a mold.

In some embodiments, an embedded sample undergoes cutting or sectioning at step 248. In some embodiments, the sample received by the laboratory is already an embedded tissue sample, which is sent straight to the cutting or sectioning operations at step 248. In some embodiments, a microtome comprising a blade is used to cut tissue sections. In some embodiments, the blade is a glass or diamond blade. In some embodiments, the sample is cut using an ultramicrotome. In some embodiments, samples are cut into sections about 2 to 15 micrometers thick.

In some embodiments, the cut sections are placed into a water bath to help tissue expand and smooth out the sections. In some embodiments, the sections are picked up onto a slide from the water bath. In some embodiments, the slide containing the section of the embedded tissue is warmed to facilitate adhesion of the sample to the slide and drying of the embedded sample.

In some embodiments, after the sample is prepared and placed on to slide, the sample is stained at step 250 to provide contrast between cell types and highlight features of interest within the sample. In some embodiments, samples are sent to the laboratory as unstained histology slides and are immediate sent to be stained at step 250. In some embodiments, a solvent is used to remove the embedding medium from the tissue. In some embodiments, the tissue sample is stained using hematoxylin and eosin (H&E stain). In some embodiments, the tissue sample is stained using an immunohistochemistry staining process wherein chromagen-labeled antibodies are bound to the tissue sample. In some embodiments, the tissue sample is stained using an immunofluorescence staining process wherein fluorescent-labeled antibodies are bound to the tissue sample. Other stains or staining methods may be utilized. In some embodiments, a coverslip is placed over the tissue samples after they have been stained.

Stained tissue samples provided on histology slides are then scanned at step 252. In some embodiments, samples are sent to the laboratory as stained histology slides and are immediate scanned at step 252. The scanned slides may then be uploaded to a database or saved to a local memory at step 254. The scanned slides may then be evaluated and analyzed at step 256 during quality control to ensure that the captured images of the slides are of high enough quality such that a proper analysis of the slides may be performed. The quality control performed at step 256 may comprise high resolution analysis of a plurality of image patches from each histology slide. In some embodiments, an automated quality control analysis utilizes a trained neural network to analyze images of the histology slides to assess the quality of the images. If a histology slide fails at the quality control step, it may be sent back to be reprocessed at any one of the sample preparation steps. In some embodiments, automated systems recognize which preparation step should be revisited in order to obtain a successful histology slide.

In some embodiments, some of the lab operations are automated. In some embodiments, all lab operations are automated. In some embodiments, automated systems are utilized to provide the tissue samples through each stage of processing. Automated systems may include conveyor belts, robotic arms, or the like, to transfer the samples between stations which the processing stages take place.

In some embodiments, identification of gross errors occurs throughout the preparation of the tissue samples. In some embodiments, identification of gross errors is accomplished by a technician trained to recognize errors or imperfections during preparation of the samples. In some embodiments, automated system utilizing cameras are setup at various locations during preparations of the tissue samples to recognize errors or imperfections during preparation of the samples. If an error or imperfection is recognized a tissue sample during processing, it may be sent back to be reprocessed at any one of the sample preparation steps. In some embodiments, automated systems recognize which preparation step should be revisited in order to correct the error or imperfection.

D. Pathology Database/Additional Services and Completion

In some embodiments, after the images of the slides are scanned, they are uploaded to a pathology database. The pathology database may be accessible to computing devices external to the network. In some embodiments, images of the slides are provided as digital zoom images.

After histology slides are scanned and reviewed for quality, the lab may provide additional services and complete the order at step 260. In some embodiments, after the slides are processed in quality control the order is considered fulfilled at step 262. In some embodiments, a turnaround time is measured from when the order/sample is received by the lab, at step 228, to when the order is considered fulfilled at step 262. In some embodiments, at step 264, additional services such as providing a pathology report and performing an image analysis are considered. In some embodiments, a pathology report is generated, at step 266, from using the digital images of the tissue samples. In some embodiments, the pathology report is provided by a technician. In some embodiments, digital images of slides are automatically tagged with labels indicating cell types for a histopathological analysis. In some embodiments, a histopathological analysis is performed by a pathologist. In some embodiments, a histopathological analysis is automated, as disclosed herein. In some embodiments, at step 268, a qualitative image analysis is performed on the digital images of the histology slides. In some embodiments, a qualitative image analysis is automated.

In some embodiments, at step 270, the order is provided to a billing system. In some embodiments, the order is held until payment is provided. In some embodiments, once payment is provided the digital images of the slides are provided to the client at step 272. In some embodiments, the images are provided as digital zoom images. In some embodiments, the images are accessible via a web application. In some embodiments, after viewing the digital images of the tissue samples, the client provides feedback at step 274. If the client does not require any changes, then the order may be marked as complete at step 276. If the client requests changes, then the request may be logged and the order may be reprocessed at step 258.

Once an order is considered complete, the samples may be shipped to the client at step 278. In some embodiments, a client must submit a request to have the samples shipped back to them. The order may then be marked as finalized, at step 280. If the client does not request the samples, then the samples may be held at the lab or disposed of, and the order will be marked as finalized.

II. Laboratory Information Management System (LIMS)

A laboratory information management system (LIMS) provides an efficient means of providing and updating the status of orders, samples, and slides to manage workflows of multiple orders. The LIMS systems also facilitates access to order and sample information, as well as access to digital images of slides corresponding to orders/samples.

In some embodiments, provided herein is laboratory information management system (LIMS). In some embodiments, the LIMS provides a staff interface (i.e., backend or administrative interface) for laboratory staff to manage orders for processing and/or analysis of samples, digital images of samples, and digital micrographs of samples. In some embodiments, the samples are stained. In some embodiments, the samples are placed onto a slide to form a histology slide.

Figure 3:
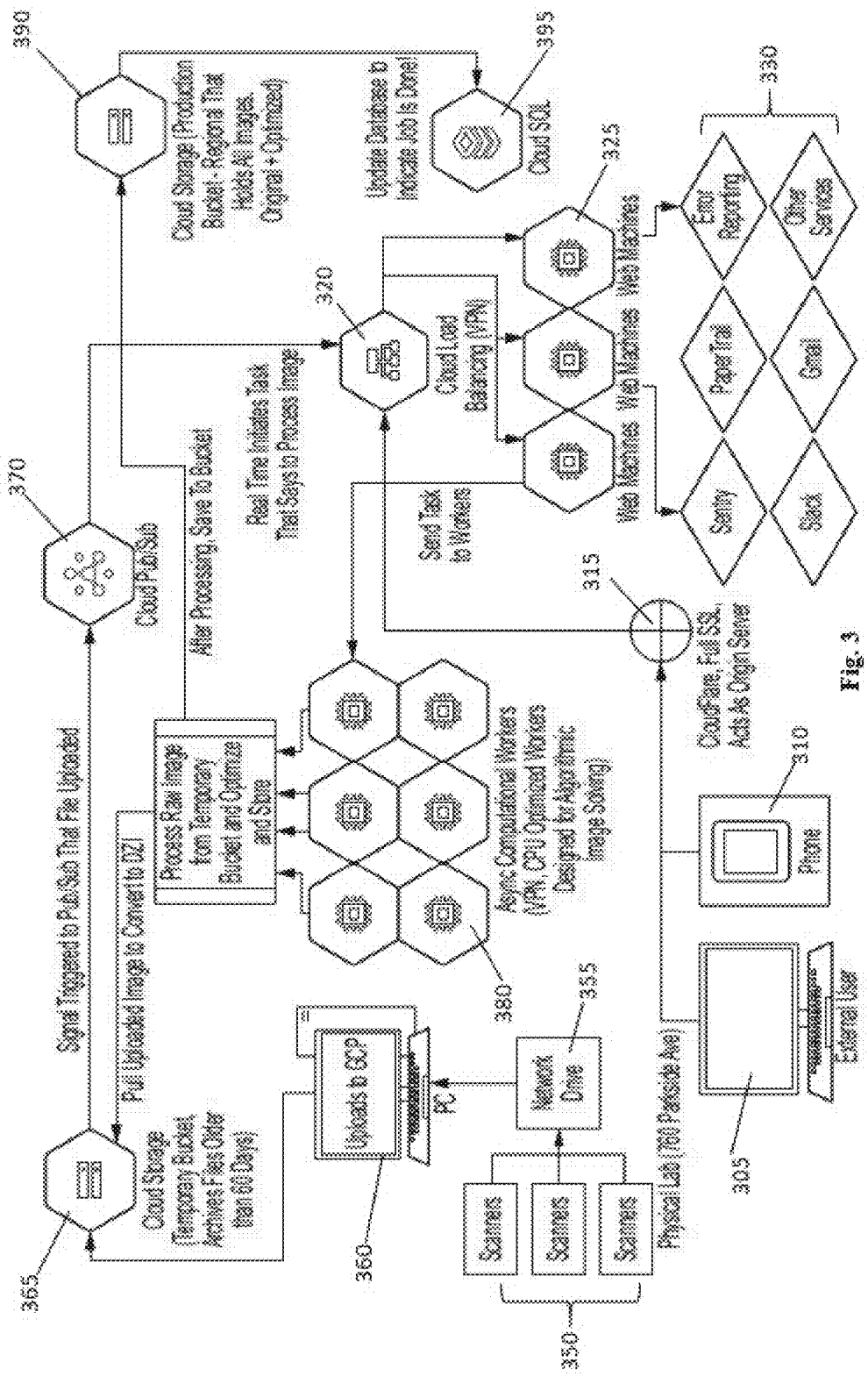
FIG. 3 depicts a non-limiting example of a lab information management system.

With reference to FIG. 3, in some embodiments, the LIMS is accessible via a computing device 305, 310 external to the LIMS. In some embodiments, the external computing device is a mobile computing device 310. In some embodiments, access to a staff interface of the LIMS requires authentication or verification. In some embodiments, single-factor authentication, two-factor authentication, multi-factor authentication, single sign-on authentication, or a combination thereof is used to access a staff interface of the LIMS.

In some embodiments, the staff interface of the LIMS provides a collection of orders which have been submitted, are in progress, and have been completed. In some embodiments, orders are categorized by their current status or state.

In some embodiments, the orders are categorized by their current status within a lab review process. This may include steps completed as part of initializing an order or lab preparation (e.g., initiation of an order 210 and/or lab preparations 220 steps as depicted by FIG. 2). In some embodiments, selectable lab review statuses include open orders, open immunofluorescence (IF) orders, in progress immunohistochemistry (IHC) staining orders, special stain orders, IHC optimization orders, late orders, unfulfilled orders, open orders due by specified date, orders which need to be assigned a turnaround time, orders which are pending, orders which need to be recut, finalized orders, and all orders. Orders may be accessible through selection one or more of the provided status categories.

In some embodiments, orders are provided by the status within the lab workflow. This may include steps completed as part of the automated histology and lab operations (e.g., lab operations 230 as depicted in FIG. 2) In some embodiments, selectable lab workflow statuses include orders which need a process review, orders which need payment, orders which have been shipped, orders which have been received, orders to be grossed, orders to be embedded, orders to be cut, orders to be stained, orders to be screened, orders ready to be filled, completed orders, and orders pending shipment. Orders may be available in one or more of the provided status categories.

In some embodiments, the orders are provided by the status within a customer service workflow. In some embodiments, selectable customer service workflow categories include orders which need image analysis or pathology consultation, orders which need client feedback, and orders which need to be invoiced or billing adjustments. Orders may be accessible through selection one or more of the provided status categories.

In some embodiments, the LIMS provides accessibility to processed samples and slides via categorization. In some embodiments, digital images of slides are categorized using metadata attributed to the slides or portions of the slides by an automated tagging system, as described herein. The metadata attributed to the slides may allow for a user to review slides which meet a search criteria. In some embodiments, metadata attributed to the slides by the automated tagging system includes, but is not limited to species, organ type, stain type, lesion type (tumor, necrosis, fibrosis, metastasis, etc.), cell type, disease type, antibodies, fixative type, gene expression, tumor type, biosystem, mouse strains, experiments, xenografts, GEMM, promoters, reporters, age, gender, and combinations thereof.

In some embodiments, selection of a sample or histology slide also allows access to the corresponding order form. In some embodiments, histology slides are categorized and accessible via the LIMS by their status in the lab workflow. In some embodiments, slide categories include slides which need a quality control review, slides which need to be recut, slides which need to be rescanned, slides which have failed any aspect of quality control, samples wherein antibody slides have been requested, samples wherein special stains have been requested, samples wherein a channel filter slide has been requested, all slides, all samples, slide comments.

In some embodiments, pathology consultation orders are accessible via the LIMS. In some embodiments, team or user management databases are also provided via the LIMS. In some embodiments, staff and team information is sorted and accessible by users, teams, team addresses, organizations, projects, and billing contacts. In some embodiments, the LIMS provides access to orders through libraries categorized by a specific user, technician, or team. IN some embodiments, the LIMS provides access to orders through libraries belonging to a specific organization, project, or billing contact. In some embodiments, the LIMS provides access to orders and slides via categorization of components utilized in preparing samples. In some embodiments, orders and slides are accessible via categorization of antibodies, antibody application, antibody attachments, sample submissions, species types, special stains, organ types, fixatives used, and immunofluorescent channel filters used.

In some embodiments, categorization and/or sorting of the orders by the above mentioned statuses/categories allows personnel to access orders which are relevant to their role or specialization. For example, a technician who specializes in grossing may select the grossing library to access all orders which are to be reviewed for gross errors in the. Upon a selection of an order, the technician may be provided with information specific to the work their role. For example, a technician who specialized in grossing will be provided with information relevant to the grossing process. The information relevant to the grossing process may be provided by a field in the order form completed by a client or a staff member.

In some embodiments, the technician is provided with selectable options to update or change the status for an order. For example, a technician specializing in cutting samples may select a 'cutting complete' button to confirm cutting of an embedded sample has been performed. In some embodiments, the LIMS provides a process history of each order. In some embodiments, the process history lists each updated or change status for an order. In some embodiments, an order process history lists the technician or staff member who made the update or change. Each status change may be recorded and presented in the process history. Each status change may provide the received status and the updated status for each instance. In some embodiments, wherein processes are automatically performed, a status change is automatically entered and recorded. In the case of an automated status change entry, the field which typically lists a technician or staff member may be entered as 'none' or 'automated'.

In some embodiments, upon selection of an order, information regarding the order is presented to the user. In some embodiments, order information includes associated samples. The LIMS may further provide information attributed to the samples such as stain/unstained, stain type, requested IHC antibody names, requested IF channels, requested pathology consultations, species type, organ type, if the sample is of a tumor, control type, indication of bone decalcification, fixation time, and cut type.

In some embodiments, updates, edits, comments, or any information input into the LIMS by a staff member triggers notifications to other team members if relevant. Notifications may be sent via email or via a business based communication system, such as slack. Notifications may be automatically triggered by submission of the information by a staff member or may be pushed by a selection made by the staff member entering the information. In some embodiments, a dedicated group of web machines 325 is responsible for pushing notifications via connected software applications.

In some embodiments, the LIMS provides a customer-facing user interface. In some embodiments, actions completed on the customer-facing or frontend interface application programing interface (API) operations will be sent to the LIMS. In some operations, actions completed in the customer-facing interface will be recorded and provided within the staff interface. In some embodiments, a customer using the frontend interface will click a button provided on the interface to save any information which has been entered in available fields of an order form. The submitted information may be immediate available to be viewed by staff on a staff or backend interface. In some embodiments, upon processing of a sample to create a digital image of a histology slides, scanned images of histology slides will be made available on the user facing interface. In some embodiments, using the staff-facing interface, a technician or staff member is able to access the digital images of the histology slides, which are available to the user, via selecting an order and selecting slides which correspond to said order. This may help facilitate the user experience.

A. Information Management System Configuration

With reference to FIG. 3, a system for analyzing digital micrographs representing a slide with a tissue sample and processing a customer order, is depicted according to some embodiments. In some embodiments, scanners 350 are provided to scan and produce digital images or a digital micrograph representing a histology slide. In some embodiments, the scanners 350 are connected to a network drive 355, such that the images obtained by the scanners 350 are uploaded to the network drive 355. In some embodiments, one or more computing devices 360 are connected to the network drive 355. In some embodiments, the computing device 360 uploads data from stored files on the network drive 355 to a cloud storage database or datastore 365. In some embodiments, the cloud storage datastore 365 is configured as a temporary storage datastore. In some embodiments, the cloud storage datastore 365 automatically achieves files after a duration of time. In some embodiments, the cloud storage datastore 365 automatically achieves files after 60 days. In some embodiments, the cloud storage datastore is provided by the Google Cloud Platform application.

In some embodiments, the system comprises an external user computing device 305 or an external mobile computing device 310. In some embodiments, the external computing device 305, 310 connects to an origin server 315. The origin server 315 connects the external computing device 305, 310 to a cloud balancing virtual private network (VPN) 320. In some embodiments, the cloud balancing VPN 320 is further connected to one or more web machines 325. In some embodiments, the web machines 325 perform tasks such as error monitoring, error reporting, sending notifications via email or other services (e.g., Slack), log significant events of the system, and create a paper trail of activates/tasks performed by the system. In some embodiments, the web machines 325 send tasks to a group of asynchronous computational devices 380.

In some embodiments, the asynchronous computational devices 380 are configured for algorithmic image solving. In some embodiments, the asynchronous computational devices 380 carry out the image processing and analysis disclosed herein. In some embodiments, the computational devices 380 analyze and detect errors or imperfections present in histology slides. In some embodiments, computational devices 380 detect levels of blurriness present in digital representations of histology slides.

In some embodiments, the computational devices 380 detect features of a tissue sample provided on a histology slide. In some embodiments, computational devices use machine learning to automatically infer metadata for a digital image of a histology slide which is stored in the LIMS. In some embodiments, the metadata includes a collection of tags or attributes that describe histology slides or portions of the tissue within the histology slides. In some embodiments, the attributed metadata enables searching through the LIMS for digital histology slide images matching a specified criteria.

In some embodiments, the computational working devices 380 are CPU optimized. In some embodiments, the computation working devices 380 comprises at least one processor, a memory, and instructions executable by the at least one processor to carry out the methods disclosed herein. In some embodiments, a plurality of computation working devices 380 each comprise at least one processor. In some embodiments, a plurality of computation working devices 380 each comprise at least one processor a memory. In some embodiments, the computational devices 380 are connected to a VPN. In some embodiments, the computational devices 380 are configured to assess high resolution image patches of histology slides.

In some embodiments, the system further comprises a communication medium 370. The communication medium 370 may be connected to the first cloud storage data base 365 and the cloud balancing VPN 320. In some embodiments, the communication medium provides the files from the first cloud storage datastore 365 to the cloud balancing VPN 320, which in turn provides files to the web machines 325, and finally to the computational devices 380 for processing. In some embodiments, the communication medium 370 is provided by Google Pub/Sub.

In some embodiments, computational devices 380 process the digital images of the histology slides to output a digital zoom image (DZI). The DZI files may be transferred to a second cloud storage datastore 390 along with the original images from the scanners. In some embodiments, a cloud server datastore 395 is updated to indicate that processing of the images is complete. In some embodiments, the cloud server datastore 395 is provided by Google Cloud SQL. In some embodiments, the DZI files are transferred to the first cloud datastore 365, through the communication medium 370, through the cloud balancing VPN 320, and processed by the web machines 325 report errors, send notifications via email or other services (e.g., Slack), log significant events of the system, and create a paper trail of activates/tasks performed by the system.

III. Automated Tagging of Histology Slides

In some embodiments, provided herein are systems and methods of tagging attributes of histology slides. In some embodiments, a computer system that uses machine learning to automatically infer metadata for a whole slide image (WSI) that is part of a slide database. In some embodiments, the slide database comprises the LIMS disclosed herein. In some embodiments, the metadata includes a collection of tags or attributes that describe a whole slide image or portions of the tissue within the whole slide image. In some embodiments, the attributed metadata enables search across a database of millions of digital slide images. Searches may be defined by attributes across an entire digital image of a histology slide. In some embodiments, searches are defined at an intra-slide level, wherein the search is defined by attributes present in regions or portions of a digital image of a histology slide.

In some embodiments, the metadata fields comprise: species, organ type, stain type, lesion type (tumor, necrosis, fibrosis, metastasis, etc.), cell type, disease type, antibodies, fixative type, gene expression, tumor type, biosystem, mouse strains, experiments, xenografts, GEMM, promoters, reporters, age, gender, and combinations thereof. In some embodiments, each metadata field contains a single Boolean representing presence/absence, a string defining the type, or a more complex data field (e.g., a proportion of the slide that matches the field attribute, specific information on where in the slide the field attribute is located, or a classification of severity).

In some embodiments, a search can be performed by matching specific attributes (e.g., find all slides with IHC stain type and mouse as the species). In some embodiments, a search can also be performed by thresholding on an attribute (e.g., find all slides where at least 30% of the tissue exhibits necrosis). In some embodiments, a search can also be defined to return regions within whole slide images (e.g., find all regions that are approximately 30×30 microns in size and contain >40% tumor and at least 50 lymphocytes). In some embodiments, a search can be defined to return regions within a single histology slide (e.g., show all regions exhibiting metastasis). In some embodiments, the attributed metadata can also be used to sort/rank search results.

In some embodiments, an attention mechanism considers the importance of each patch of a plurality of patches to integrate patch-level information and automatically locate of regions of interest. In some embodiments, an attention mechanism utilizes multi-instance learning to highlight patch instances that contribute the most to slide-level classification. In some embodiments, a graph convolutional network (GCN) is utilized to learn attention weights for each patch.

In some embodiments, given a WSI dataset $I=\{I_1, \ldots, I_n\}$ where each $I_n$ is a whole slide image, groups or bags of patches $B=\{B_1, \ldots, B_n\}$ where each $B_n$ is a bag of M sampled patches from regions of the slide containing a tissue sample (i.e., the non-background regions of $I_n$). In some embodiments, K sets of tags $C_k$ each have multiple classes. In some embodiments, the whole slide images (I), comprise corresponding Kth tags can be represented as $L_k=\{L_{k1}, \ldots, L_{kn}\}$, where $L_{kn} \in C_k$. Ideally, all K tags are correctly assigned for each image.

Figure 4:
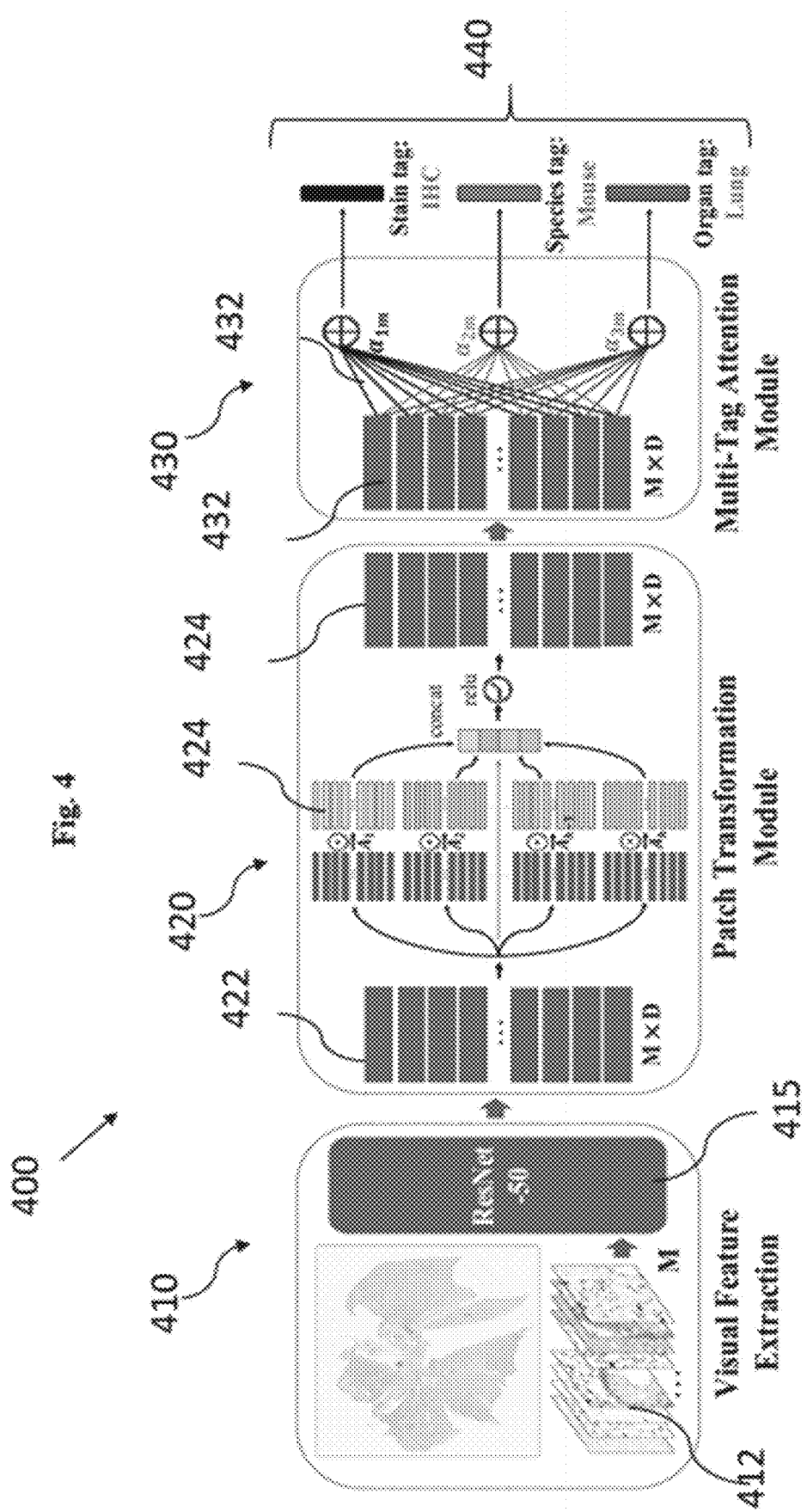
FIG. 4 depicts a non-limiting example of a system for automated classification of histology slides.

In some embodiments, a patch transformation module is utilized to learn patch characteristics by considering global patch contexts. In some embodiments, with reference to FIG. 4, a machine learning model 400 for predicting multiple slide-level tags comprises a visual feature extraction module 410, a patch transformation module 420, and a multi-tag attention module 430.

In some embodiments, the visual feature extraction module 410 is configured to extract a visual feature representation of each patch. In some embodiments, the visual feature extraction module takes as inputs from latent visual embeddings 412 extracted by a ResNet network 415. In some embodiments, the ResNet network comprises ResNet-34, ResNet-50, or ResNet-101. In some embodiments, the visual feature extraction module 410 then maps each patch feature into different attention domains through multi-head attentions. In some embodiments, final feature outputs are the aggregation of the obtained representations.

In some embodiments, a patch transformation module 420 is configured to modulate patch features by providing the extracted visual feature representations as inputs 422 to a first attention aggregation mechanism 424. In some embodiments, a first attention aggregation model 422 maps each visual feature representation into different attention-weighted features through multi-head attentions and outputs a weighted patch feature 426 comprising an aggregation of the visual feature representations and the attention-weighted features.

In some embodiments, the multi-tag attention module 430 is configured to construct slide-level tags identifying tag classifications 440. In some embodiments, slide-level tag classifications are identified by providing weighted patch features 432 to a plurality of second attention aggregation mechanisms 434. In some embodiments, one attention aggregation mechanism is provided per output head. In some embodiments, each of the second attention aggregation mechanisms performs operations comprising: mapping each weighted patch feature into different attention-weighted features through multi-head attentions, and outputting a slide-level tag comprising an aggregation of the attention-weighted features. In some embodiments, the machine learning model operates in a multi-scale mode utilizing the patches at the plurality of magnifications to identify both patch features and magnification levels most discriminant for the multi-tagging.

In some embodiments, for the visual embedding $V \in \mathbb{R}^{M \times D}$, the output of the module can be represented by:

$$V = \sigma(V + W^T[f_1, \ldots, f_h]), V \in \mathbb{R}^{M \times D}, W \in \mathbb{R}^{(h \times D) \times D} \quad (1)$$

In some embodiments h represents the hth head in the module, $\sigma(\cdot)$ is the ReLU non-linear activation function. Each $f_h$ is a feature extracted by an attention unit. In some embodiments, different patches share the same attribute tags. In some embodiments, the multi-head computation as an attention is formulated as an aggregation process to obtain characteristic-enhanced feature representations for informative patch selection. In some embodiments, for the extracted patch feature matrix V, element-wise multiplication is performed between V and multi-head patch attention matrices, i.e., $f_h = V \odot A_h$, $V, A_h \in \mathbb{R}^{M \times D}$. The attention matrix $A_h$ May be written as $A_h = [a_h, a_h, \ldots, a_h]$, where each column $a_h E \in \mathbb{R}^{M \times 1}$ is a duplicate of the attention vector for the patch features. In some embodiments, each weight in $a_h$ is calculated by $$a_{hm} = \text{Softmax}(W_h^T \tan h(U_h^T v_m)), W h \in \mathbb{R}^{D \times 1}, U_h \in \mathbb{R}^{D \times D}, v_n \in \mathbb{R}^{D \times 1} \quad (2)$$

In some embodiments, a residual connection is added from the output and directly aggregated with each patches weighted representation (Eq. 1). In some embodiments, this allows each patch feature's distinct characteristics while at the same time preserving its original feature representation. In some embodiments, the final output is obtained by applying the ReLU non-linear activation function.

In some embodiments, there exists correlations among different tags (e.g., most Zebrafish slides are H&E stained) which makes multi-task learning an appropriate approach. In some embodiments, different tags focus not only on common regions but also on tag-specific regions which results in different potential regions of interest (ROIs). A multi-tag attention module 430 may be utilized to learn each tag's region of interest adaptively and to form tag-related slide level representations. In some embodiments, the multi-tag attention module 430 adopts the same attention mechanism as used in the previously introduced patch transformation module except that the output is obtained by aggregating weighted patch features. In some embodiments, this allows the model to leverage the previously learned patch characteristics to assign tag-related weights. In some embodiments, the tag-specific representations can be represented by $$T_k = \sum_{m=1}^{M} \alpha_{km} \times v'_m$$

where k represents the kth tag. In some embodiments, $v'_n \in \mathbb{R}^{D \times 1}$ is a patch feature in V, $\alpha_{km} \times v'_m$ is a tag-related weight scalar and is computed following the same format in equation (2). In some embodiments, the prediction probability for each tag of each WSI is computed by $$\hat{l}_k = \text{Softmax}(w_k^T t_k), W_k \in \mathbb{R}^{D \times D_k}, t_k \in \mathbb{R}^{D \times 1} \quad (3)$$

In some embodiments, $D_k$ represents the number of classes in $C_k$. In some embodiments, the model is end-to end trained with a combination of multi-class cross entropy losses (CE) for each tag weighted by $\lambda_k$ $$\mathcal{L} = \sum_{k=1}^{K} \lambda_k \mathcal{L}_k = \sum_{k=1}^{K} \lambda_k \frac{1}{N} \sum_{n=1}^{N} CE(l_{kn}, \hat{l}_k) \quad (4)$$

In some embodiments, attribution of metadata is improved by utilizing patch sizes at a range of magnifications. In some embodiments, this enables the model to adaptively learn which magnifications are most useful for a specific classification task via the attention mechanism within the model. In some embodiments, the model was enhanced by enabling training on incomplete data. In many situations, the metadata for slides is incomplete. In some embodiments, the model handles partially missing data by modulating the loss function used in training the neural network. Attributes that are missing have a weaker or negligent impact on the loss.

A. Multi-Scale Tagging

In some embodiments, for many of the metadata fields, the attribute is not a property of the WSI as a whole, but rather something that can occur at various locations and with various spatial densities or levels of severity throughout a histology slide. In some embodiments, one or more fully convolutional neural networks to produce a heatmap of where the attribute of interest is located within an image region. In some embodiments, the heatmap is a pixel-wise prediction between 0 and 1 that represents the probability of the attribute being present at that pixel location. In some embodiments, the image region is generally extracted from the WSI at a specific magnification level that is appropriate for the attribute being identified. In some embodiments, the WSI is sampled at multiple magnification levels. In some embodiments, WSIs are sampled at a first magnification level, a second magnification level, a third magnification level, a fourth magnification level, a fifth magnification level, a sixth magnification level, a seventh magnification level, an eighth magnification level, a ninth magnification level, etc.

In some embodiments, the magnification level is between 4× and 100×. In some embodiments, the magnification level is about 4× to about 200×, including increments therein. In some embodiments, the magnification level is about 4× to about 5×, about 4× to about 10×, about 4× to about 20×, about 4× to about 40×, about 4× to about 50×, about 4× to about 70×, about 4× to about 100×, about 4× to about 150×, about 4× to about 200×, about 5× to about 10×, about 5× to about 20×, about 5× to about 40×, about 5× to about 50×, about 5× to about 70×, about 5× to about 100×, about 5× to about 150×, about 5× to about 200×, about 10× to about 20×, about 10× to about 40×, about 10× to about 50×, about 10× to about 70×, about 10× to about 100×, about 10× to about 150×, about 10× to about 200×, about 20× to about 40×, about 20× to about 50×, about 20× to about 70×, about 20× to about 100×, about 20× to about 150×, about 20× to about 200×, about 40× to about 50×, about 40× to about 70×, about 40× to about 100×, about 40× to about 150×, about 40× to about 200×, about 50× to about 70×, about 50× to about 100×, about 50× to about 150×, about 50× to about 200×, about 70× to about 100×, about 70× to about 150×, about 70× to about 200×, about 100× to about 150×, about 100× to about 200×, or about 150× to about 200×, including increments therein. In some embodiments, the magnification level is about 4×, about 5×, about 10×, about 20×, about 40×, about 50×, about 70×, about 100×, about 150×, or about 200×, including increments therein. In some embodiments, the magnification level is at least about 4×, about 5×, about 10×, about 20×, about 40×, about 50×, about 70×, about 100×, or about 150×, including increments therein.

Figure 5:
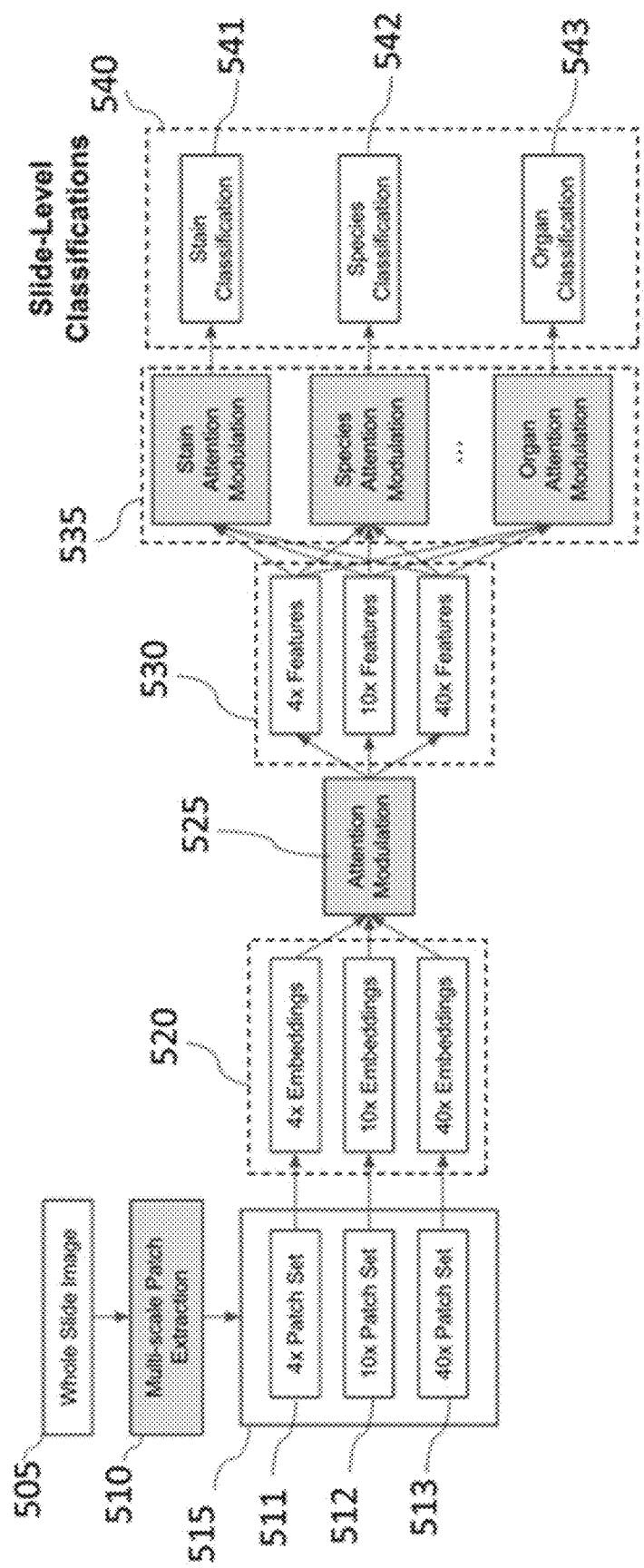
FIG. 5 depicts a non-limiting example of a method for automated classification of histology slides.

With reference to FIG. 5, a Multi-Scale tagging method is depicted, according to some embodiments. In some embodiments, a digital image of a histology slide 505 is provided at a step 505. The digital image of the histology slide may be a digital micrograph representing a histology slide. The digital image of the histology slide may be obtained by using the systems and methods disclosed herein. The digital image of the histology slide may be provided by a laboratory management information system (LIMS).

In some embodiments, at step 510, the whole slide image (WSI) is processed by a first module for extraction of visual feature representations. In some embodiments, processing by the visual feature extraction module includes sampling a plurality of non-background patches from the WSI at a plurality of magnifications. In some embodiments, the WSI is sampled prior to being submitted to the visual feature extraction module.

In some embodiments, the sampled patches are output at step 515. In some embodiments, the visual feature extraction module outputs the sample patches at step 515. In some embodiments, the sample patches are grouped by their magnification level. For example, sample patches may be grouped in a first magnification 511 of 4×, a second magnification 512 of 10×, and a third magnification 513 of 40×.

In some embodiments, the visual feature extraction module extracts a visual feature representation of each patch. In some embodiments, at step 520, latent visual embeddings are extracted from the sample patches. In some embodiments, the embeddings are grouped by their respective magnification levels. In some embodiments the latent visual embeddings are extracted by a ResNet network. In some embodiments, the ResNet network comprises ResNet-34, ResNet-50, or ResNet-101.

In some embodiments, at step 525, the latent visual embeddings are input into a second module for mapping each visual feature representation into different attention-weighted features through multi-head attentions and outputting a weighted patch feature comprising an aggregation of the visual feature representations and the attention-weighted features. The second module may be referred to as an attention aggregation module or mechanism, as disclosed herein. In some embodiments, the attention aggregation module performs operations comprising: mapping each visual feature representation into different attention-weighted features through multi-head attentions and outputting a weighted patch feature comprising an aggregation of the visual feature representations and the attention-weighted features. In some embodiments, the machine learning model operates in a multi-scale mode utilizing the patches at the plurality of magnifications to identify both patch features and magnification levels most discriminant for the multi-tagging.

In some embodiments, the attention aggregation module outputs weighted patch features, at step 530. In some embodiments, the weighted patch features are input into a third module, a step 535. In some embodiments, the third module is configured to construct slide-level tags identifying tag classifications by providing the weighted patch features to a plurality of second attention aggregation mechanisms. In some embodiments, a second attention aggregation module is provided for each classification type or output head. In some embodiments, each of the second attention aggregation modules each perform operations comprising: mapping each weighted patch feature into different attention-weighted features through multi-head attentions, and outputting a slide-level tag comprising an aggregation of the attention-weighted features, at a step 540. In some embodiments, the third module associates multiple slide-level tags with the digital whole slide image. In some embodiments, the slide-level tags are associated with a classification. In some embodiments, each slide is associated with a first classification, a second classification, a third classification, a fourth classification, a fifth classification, a sixth classification, a seventh classification, an eighth classification, a ninth classification, etc. For example, a first classification 541 may comprise a stain type classification, a second classification 542 may comprise a species type classification, and a third classification 543 may comprise an organ type classification. In some embodiments, the classifications input into metadata fields associated with the digital slides.

Figure 6:
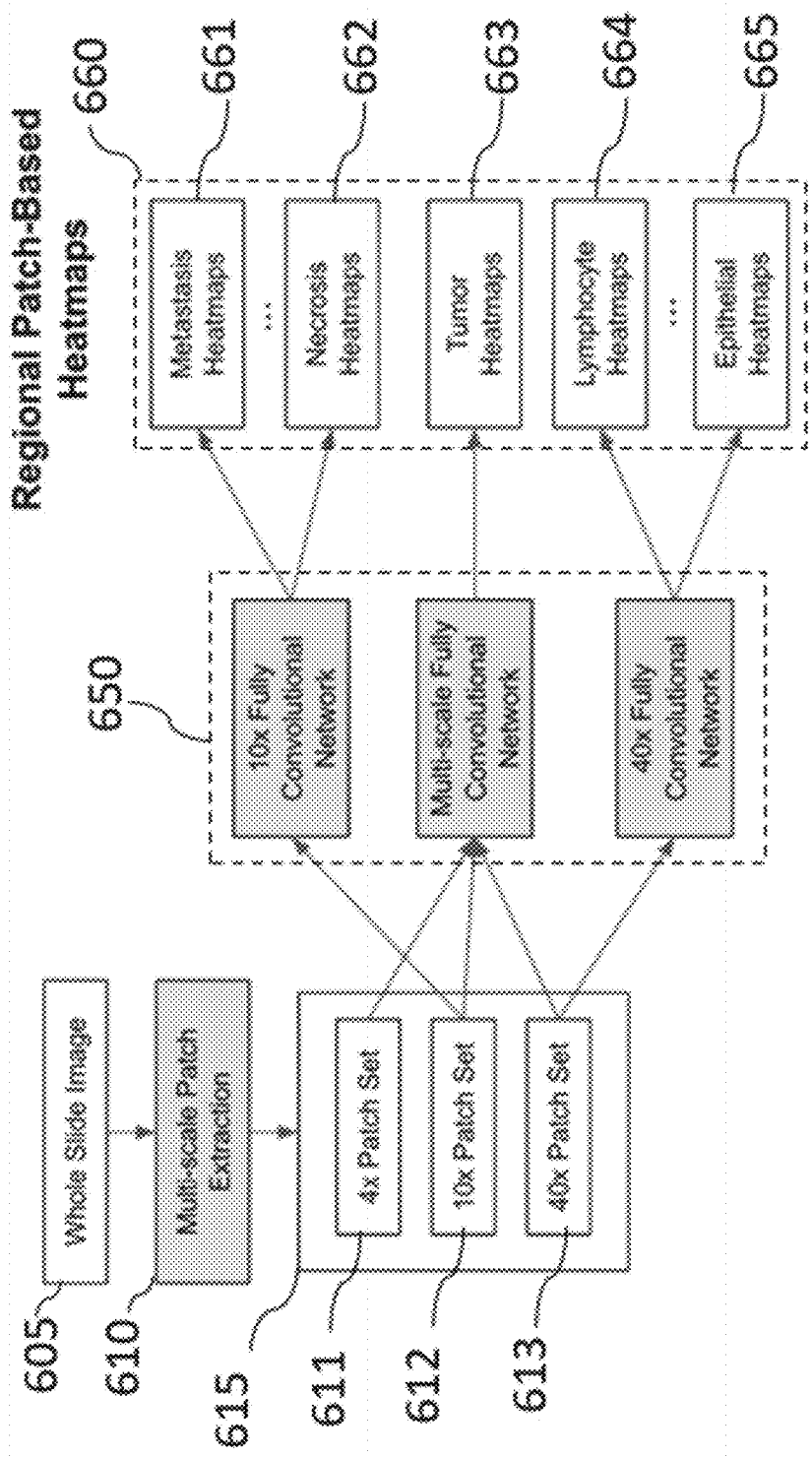
FIG. 6 depicts a non-limiting example of a method for producing heatmaps for histology slides.

With reference to FIG. 6, a method of processing whole slide images to produce regional patch-based heatmaps is depicted. In some embodiments, heatmaps are used to classify regions of a whole slide image. In some embodiments, the method comprises receiving a whole slide image at step 605. In some embodiments, the method comprises sampling a plurality of non-background patches from the whole slide image or the portion thereof at a plurality of magnifications. In some embodiments, the sampled patches comprise patches at a plurality of magnification, such as a first magnification level 611, a second magnification level 612, and a third magnification level 613.

In some embodiments, a visual feature extraction module extracts a visual feature representation of each patch, at step 615. At step 650, a second module configured to apply one or more neural networks using the visual feature representations of the patches as inputs to produce a heatmap. In some embodiments, the one or more neural networks comprise a multi-scale convolutional network. In some embodiments, the one or more neural networks comprise a convolutional network at for a specific magnification level. One or more neural networks may comprise a combination of a multi-scale convolutional network and specific scale convolution networks. For example, the one or more neural networks may comprise a 10× magnification convolutional network, a multi-scale convolutional network, and a 40× magnification convolutional network.

In some embodiments, the one or more neural networks output one or more heatmaps, at step 660. Heatmaps may include a first heatmap 661, a second heatmap 662, a third heatmap 663, fourth heatmap 664, a fifth heatmap 665, etc. In some embodiments, the heatmaps demonstrate where multi-tagging attributes of interest are located within the whole slide image or the portion thereof. In some embodiments, the heatmaps demonstrate locations of a lesion type, such as comprises a tumor, necrosis, fibrosis, and metastasis. In some embodiments, a third module is configured to construct tags identifying tag classifications and distributions based on the heatmap and associate the multiple tags with the digital whole slide image or the portion thereof.

In some embodiments, the output resolution of the heatmap matches the region resolution. In some embodiments, the output resolution is downsampled version (e.g., if the region is 1000×1600 pixels, the output heatmap could be 1000×1600 pixels or if downsampled by a factor of 4, it would be 250×400). In some embodiments, the output heatmap could be downsampled to a 1×1 region, in which case it is a simple classification for that region. An output heatmap may also have multiple dimensions that correspond to different attributes being predicted (e.g., each pixel in the output might have 8 probabilities associated with it for 8 different attributes). In some embodiments, the heatmap is further processed to extract coherent regions which are then described by coordinates using a polygon, bounding box, single point, or a combination thereof. In some embodiments, a variation of the convolutional model is used to directly predict a bounding box, polygon or point (i.e., it learns to make this prediction directly rather than requiring a post-processing step).

In some embodiments, the attribute models are trained using a set of images which are regions extracted from WSIs at the appropriate magnification or at multiple magnifications when using a multi-scale model. In some embodiments, human annotators are used to identify the portions of the image that should be identified by the model. The annotations may be any of the following: bounding box, polygon, point, or freehand outline of the relevant portion, including combinations thereof. Annotated portions may also have additional metadata such as the severity of the attribute at that location. In some cases, the dataset may only be partially annotated. In some embodiments, the model modulates the loss for the unannotated areas.

In some embodiments, once one or more models are trained, they can be applied to a WSI by iteratively applying the models to regions extracted from the WSI. The regions may be extracted in such a way that the whole WSI is covered and a heatmap is thus obtained for the entire WSI. In some embodiments, the regions are distributed over the WSI to cover a certain percentage of the slide or tissue. In some embodiments, the output heatmap covers only a subset of the slide. In some embodiments, the deployment of these models typically first involves a stage to detect the tissue regions of the slide. In some embodiments, after these regions are detected, subsequent model processing is only applied to those regions.

In some embodiments, the model predicted metadata for each slide is stored and indexed in a database for later retrieval. In some embodiments, for heatmap outputs, the raw heatmap is stored. In some embodiments, other features are extracted from the heatmap such percent of tissue that exhibits the attribute. In some embodiments, this is computed by setting a probability threshold and determining the percent of the heatmap that is greater than the threshold. In some embodiments, when a tissue mask is available, the percentage may only be applied to tissue regions. The extra features may also include the following: overall area of the attribute, area measurements across a range of probability thresholds, density measurements of the attribute (i.e., is it evenly distributed across the slide or all clumped in one area), cooccurrence with other localized attributes. In some embodiments, any of these derivative features can then be used to search at the whole slide level.

In some embodiments, to enable faster region-based search within and across WSIs, the heatmap properties and derivative features are indexed for sub regions within the slide at several different levels of magnification. This may support searches across a flattened version of all regions in the WSI database and also a hierarchical search that narrows in on specific regions by iteratively searching through the index starting regions at low magnification and progressing to regions with higher magnification. In some embodiments, for region-based search, the final region returned is in some cases adjusted using the original output heatmap and derivative features for that region and adjacent regions to obtain a cropping that is most relevant for the search.

In some embodiments, the system supports a form of reverse image search that is guided by the model derived attributes. In some embodiments, given a specific region being viewed in a slide, the system is able to extract the comprehensive metadata that describes that patch. In some embodiments, a search across the index can then be performed to obtain other regions with similar metadata values. Additionally, the metadata for the region may be shown to the user along with the standard region-based search UI to help structure a relevant search to find similar regions.

IV. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a," "an," and "the" include plural references unless the context clearly dictates otherwise. For example, the term "a sample" includes a plurality of samples, including mixtures thereof.

As used herein, the term "about" a number refers to that number plus or minus 10% of that number. The term "about" a range refers to that range minus 10% of its lowest value and plus 10% of its greatest value.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

The term "in vivo" is used to describe an event that takes place in a subject's body.

The term "ex vivo" is used to describe an event that takes place outside of a subject's body. An ex vivo assay is not performed on a subject. Rather, it is performed upon a sample separate from a subject. An example of an ex vivo assay performed on a sample is an "in vitro" assay.

The term "in vitro" is used to describe an event that takes places contained in a container for holding laboratory reagent such that it is separated from the biological source from which the material is obtained. In vitro assays can encompass cell-based assays in which living or dead cells are employed. In vitro assays can also encompass a cell-free assay in which no intact cells are employed.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

The section headings used herein are for organizational purposes only and are not to be construed as limiting the subject matter described.

Computing System

Figure 1:
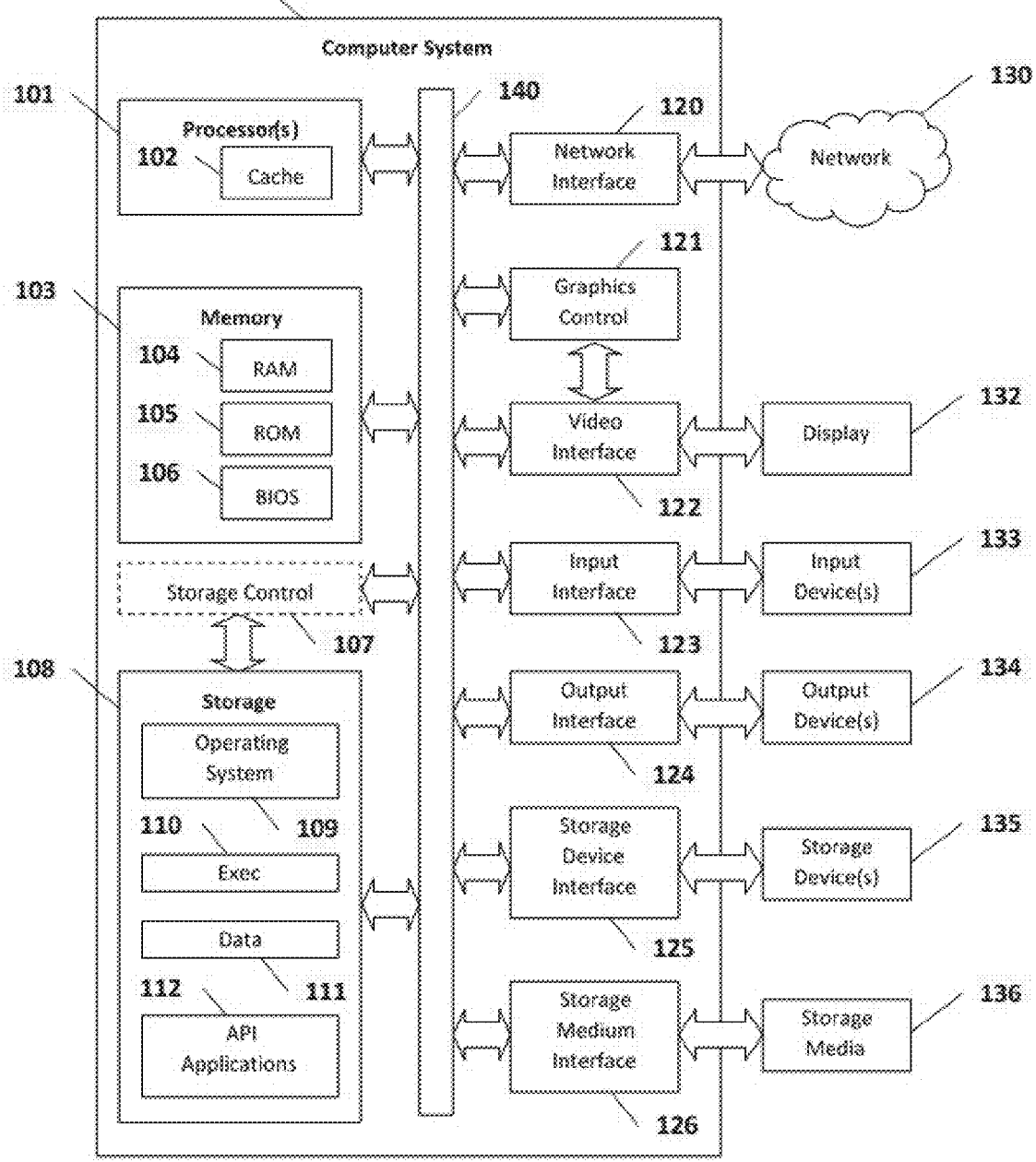
FIG. 1 shows a non-limiting example of a computing device; in this case, a device with one or more processors, memory, storage, and a network interface.

Referring to FIG. 1, a block diagram is shown depicting an exemplary machine that includes a computer system 100 (e.g., a processing or computing system) within which a set of instructions can execute for causing a device to perform or execute any one or more of the aspects and/or methodologies for static code scheduling of the present disclosure. The components in FIG. 1 are examples only and do not limit the scope of use or functionality of any hardware, software, embedded logic component, or a combination of two or more such components implementing particular embodiments.

Computer system 100 may include one or more processors 101, a memory 103, and a storage 108 that communicate with each other, and with other components, via a bus 140. The bus 140 may also link a display 132, one or more input devices 133 (which may, for example, include a keypad, a keyboard, a mouse, a stylus, etc.), one or more output devices 134, one or more storage devices 135, and various tangible storage media 136. All of these elements may interface directly or via one or more interfaces or adaptors to the bus 140. For instance, the various tangible storage media 136 can interface with the bus 140 via storage medium interface 126. Computer system 100 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Computer system 100 includes one or more processor(s) 101 (e.g., central processing units (CPUs), general purpose graphics processing units (GPGPUs), or quantum processing units (QPUs)) that carry out functions. Processor(s) 101 optionally contains a cache memory unit 102 for temporary local storage of instructions, data, or computer addresses. Processor(s) 101 are configured to assist in execution of computer readable instructions. Computer system 100 may provide functionality for the components depicted in FIG. 1 as a result of the processor(s) 101 executing non-transitory, processor-executable instructions embodied in one or more tangible computer-readable storage media, such as memory 103, storage 108, storage devices 135, and/or storage medium 136. The computer-readable media may store software that implements particular embodiments, and processor(s) 101 may execute the software. Memory 103 may read the software from one or more other computer-readable media (such as mass storage device(s) 135, 136) or from one or more other sources through a suitable interface, such as network interface 120. The software may cause processor(s) 101 to carry out one or more processes or one or more steps of one or more processes described or illustrated herein. Carrying out such processes or steps may include defining data structures stored in memory 103 and modifying the data structures as directed by the software.

The memory 103 may include various components (e.g., machine readable media) including, but not limited to, a random access memory component (e.g., RAM 104) (e.g., static RAM (SRAM), dynamic RAM (DRAM), ferroelectric random access memory (FRAM), phase-change random access memory (PRAM), etc.), a read-only memory component (e.g., ROM 105), and any combinations thereof. ROM 105 may act to communicate data and instructions unidirectionally to processor(s) 101, and RAM 104 may act to communicate data and instructions bidirectionally with processor(s) 101. ROM 105 and RAM 104 may include any suitable tangible computer-readable media described below. In one example, a basic input/output system 106 (BIOS), including basic routines that help to transfer information between elements within computer system 100, such as during start-up, may be stored in the memory 103.

Fixed storage 108 is connected bidirectionally to processor(s) 101, optionally through storage control unit 107. Fixed storage 108 provides additional data storage capacity and may also include any suitable tangible computer-readable media described herein. Storage 108 may be used to store operating system 109, executable(s) 110, data 111, applications 112 (application programs), and the like. Storage 108 can also include an optical disk drive, a solid-state memory device (e.g., flash-based systems), or a combination of any of the above. Information in storage 108 may, in appropriate cases, be incorporated as virtual memory in memory 103.

In one example, storage device(s) 135 may be removably interfaced with computer system 100 (e.g., via an external port connector (not shown)) via a storage device interface 125. Particularly, storage device(s) 135 and an associated machine-readable medium may provide non-volatile and/or volatile storage of machine-readable instructions, data structures, program modules, and/or other data for the computer system 100. In one example, software may reside, completely or partially, within a machine-readable medium on storage device(s) 135. In another example, software may reside, completely or partially, within processor(s) 101.

Bus 140 connects a wide variety of subsystems. Herein, reference to a bus may encompass one or more digital signal lines serving a common function, where appropriate. Bus 140 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 100 may also include an input device 133. In one example, a user of computer system 100 may enter commands and/or other information into computer system 100 via input device(s) 133. Examples of an input device(s) 133 include, but are not limited to, an alphanumeric input device (e.g., a keyboard), a pointing device (e.g., a mouse or touchpad), a touchpad, a touch screen, a multi-touch screen, a joystick, a stylus, a gamepad, an audio input device (e.g., a microphone, a voice response system, etc.), an optical scanner, a video or still image capture device (e.g., a camera), and any combinations thereof. In some embodiments, the input device is a Kinect, Leap Motion, or the like. Input device(s) 133 may be interfaced to bus 140 via any of a variety of input interfaces 123 (e.g., input interface 123) including, but not limited to, serial, parallel, game port, USB, FIREWIRE, THUNDERBOLT, or any combination of the above.

In particular embodiments, when computer system 100 is connected to network 130, computer system 100 may communicate with other devices, specifically mobile devices and enterprise systems, distributed computing systems, cloud storage systems, cloud computing systems, and the like, connected to network 130. Communications to and from computer system 100 may be sent through network interface 120. For example, network interface 120 may receive incoming communications (such as requests or responses from other devices) in the form of one or more packets (such as Internet Protocol (IP) packets) from network 130, and computer system 100 may store the incoming communications in memory 103 for processing. Computer system 100 may similarly store outgoing communications (such as requests or responses to other devices) in the form of one or more packets in memory 103 and communicated to network 130 from network interface 120. Processor(s) 101 may access these communication packets stored in memory 103 for processing.

Examples of the network interface 120 include, but are not limited to, a network interface card, a modem, and any combination thereof. Examples of a network 130 or network segment 130 include, but are not limited to, a distributed computing system, a cloud computing system, a wide area network (WAN) (e.g., the Internet, an enterprise network), a local area network (LAN) (e.g., a network associated with an office, a building, a campus or other relatively small geographic space), a telephone network, a direct connection between two computing devices, a peer-to-peer network, and any combinations thereof. A network, such as network 130, may employ a wired and/or a wireless mode of communication. In general, any network topology may be used.

Information and data can be displayed through a display 132. Examples of a display 132 include, but are not limited to, a cathode ray tube (CRT), a liquid crystal display (LCD), a thin film transistor liquid crystal display (TFT-LCD), an organic liquid crystal display (OLED) such as a passive-matrix OLED (PMOLED) or active-matrix OLED (AMOLED) display, a plasma display, and any combinations thereof. The display 132 can interface to the processor(s) 101, memory 103, and fixed storage 108, as well as other devices, such as input device(s) 133, via the bus 140. The display 132 is linked to the bus 140 via a video interface 122, and transport of data between the display 132 and the bus 140 can be controlled via the graphics control 121. In some embodiments, the display is a video projector. In some embodiments, the display is a head-mounted display (HMD) such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In addition to a display 132, computer system 100 may include one or more other peripheral output devices 134 including, but not limited to, an audio speaker, a printer, a storage device, and any combinations thereof. Such peripheral output devices may be connected to the bus 140 via an output interface 124. Examples of an output interface 124 include, but are not limited to, a serial port, a parallel connection, a USB port, a FIREWIRE port, a THUNDERBOLT port, and any combinations thereof.

In addition or as an alternative, computer system 100 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices include, by way of non-limiting examples, cloud computing platforms, distributed computing systems, server computers, desktop computers, laptop computers, notebook computers, sub-notebook computers, netbook computers, computers, set-top computers, media streaming devices, handheld computers, Internet appliances, mobile smartphones, tablet computers, and personal digital assistants.

In some embodiments, the computing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smartphone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux® and Palm® WebOS®.

Non-Transitory Computer Readable Storage Medium

In some embodiments, the platforms, systems, media, and methods disclosed herein include one or more non-transitory computer readable storage media encoded with a program including instructions executable by the operating system of an optionally networked computing device. In further embodiments, a computer readable storage medium is a tangible component of a computing device. In still further embodiments, a computer readable storage medium is optionally removable from a computing device. In some embodiments, a computer readable storage medium includes, by way of non-limiting examples, CD-ROMs, DVDs, flash memory devices, solid state memory, magnetic disk drives, magnetic tape drives, optical disk drives, distributed computing systems including cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable by one or more processor(s) of the computing device's CPU, written to perform a specified task. Computer readable instructions may be implemented as program modules, such as functions, objects, Application Programming Interfaces (APIs), computing data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, XML, and document oriented database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous JavaScript and XML (AJAX), Flash® ActionScript, JavaScript, or Silverlight®. In some embodiments, a web application is written to some extent in a server-side coding language such as Active Server Pages (ASP), ColdFusion®, Perl, Java™ JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile computing device. In some embodiments, the mobile application is provided to a mobile computing device at the time it is manufactured. In other embodiments, the mobile application is provided to a mobile computing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Java™, JavaScript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and PhoneGap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET or combinations thereof. Compilation is often performed, at least in part, to create an executable program. In some embodiments, a computer program includes one or more executable complied applications.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on a distributed computing platform such as a cloud computing platform. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of digital images of histology slides, results of a computational analysis, automated tagging of histology slides, automated entry of metadata for whole slide images or portions thereof, storage of metadata for whole slide images or portions thereof, and storage and retrieval of order forms for processing and analysis of tissue samples. In various embodiments, suitable databases include, by way of non-limiting examples, relational databases, non-relational databases, object oriented databases, object databases, entity-relationship model databases, associative databases, XML databases, and document oriented databases. Further non-limiting examples include SQL, PostgreSQL, MySQL, Oracle, DB2, Sybase, and MongoDB. In some embodiments, a database is Internet-based. In further embodiments, a database is web-based. In still further embodiments, a database is cloud computing-based. In a particular embodiment, a database is a distributed database. In other embodiments, a database is based on one or more local computer storage devices.

V. Examples

The following examples are included for illustrative purposes only and are not intended to limit the scope of the present subject matter.

Results of an Exemplary Multi-Tagging Model

Figure 7:
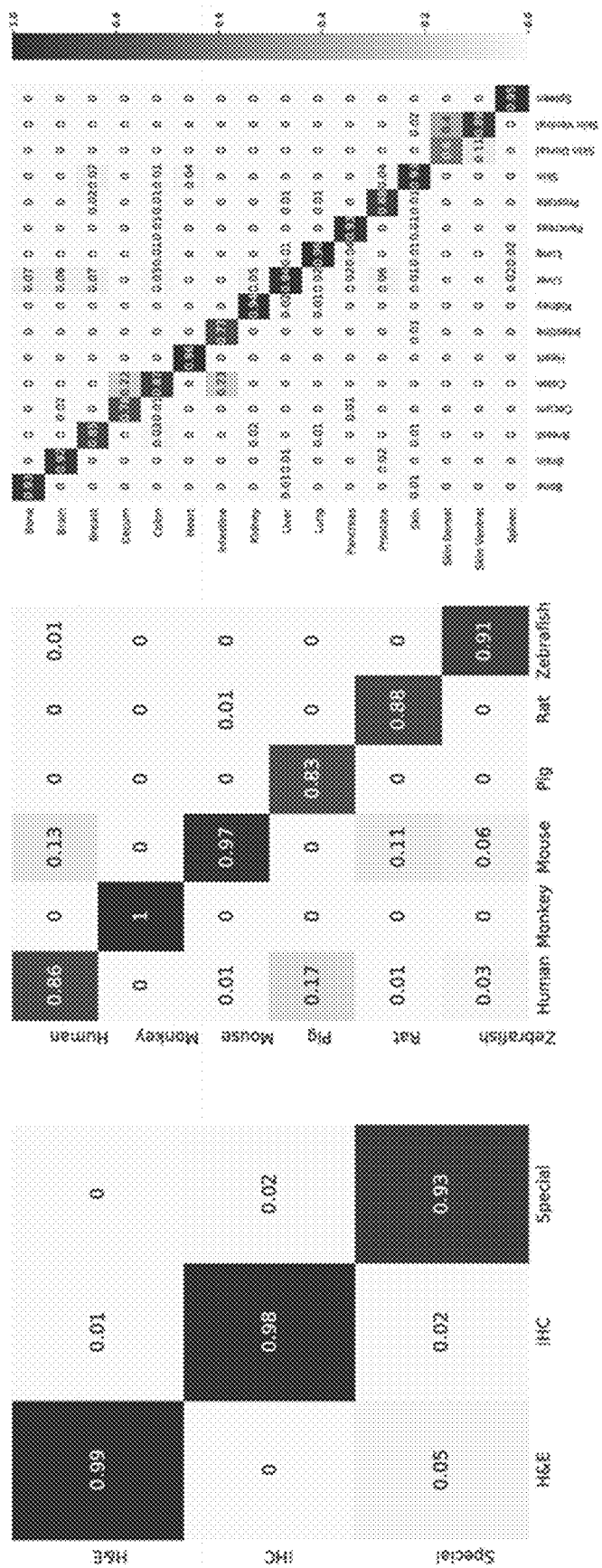
FIG. 7 depicts a non-limiting example of a normalized confusion matrices for classification of histology slides.

FIG. 7 depicts normalized confusion matrices of a model for classification of stain tag, species tag, and organ tag. In some embodiments, the stain tag comprises a 3×3 matrix. In some embodiments, the stain classifications include, but are not limited to, H&E, IHC, and special stain types. In some embodiments, the species tag comprises a 6×6 matrix. In some embodiments, the species classifications include, but are not limited to, human, monkey, mouse, pig, rat, and zebrafish species types. In some embodiments, the organ tag comprises a 16×16 matrix. In some embodiments, the organ classifications include, but are not limited to bone, brain, breast, cecum, colon, heart, intestine, kidney, liver, lung, pancreas, prostate, skin, skin dorsal, skin ventral, and spleen organ types.

In an exemplary experiment, 4920 whole slide images (WSIs) were randomly split into training and testing sets with an 8:2 ratio. 10 percent of the training data was randomly picked and kept as the validation set for model and parameter tuning. For each whole slide image, a 40× resolution was utilized and the Otsu method on the grayscale image was applied to remove background regions. During training, M=32 image patches of size 512×512 from the non-background regions were randomly extracted. Due to the class imbalance problem and the variety of the samples, rich data augmentation operations were conducted including random cropping, left-right/bottom-up flipping, and rotating. The final patch inputs are of size 224×224. In the exemplary experiment, the 2048 dimensional outputs of conv5_3 of the ResNet 50 were used as the latent visual embeddings. The ResNet 50 is pretrained on ImageNet and finetuned during the training process. The model was implemented based on Tensorflow and trained with the Adam optimizer with lr=0.0001, $\beta_1$=0.9, $\beta_2$=0.999, and $\lambda_1$=$\lambda_2$=$\lambda_3$=1.

The accuracy of the algorithm and methods used in the example are depicted in FIG. 7. The algorithm utilized in the example correctly identified H&E stain types with 99% accuracy, IHC stain types with 98% accuracy, and identified other special stain types with a 93% accuracy. In the example, the algorithm identified a species type with at least an 83% accuracy. In the example, human species tags were identified with 86% accuracy, monkey species tags were identified with 100% accuracy, mouse species tags were identified with 97% accuracy, pig species tags were identified with 83% accuracy, rat species tags were identified with 88% accuracy, and zebrafish species tags were identified with 91% accuracy. In the example, the algorithm identified an organ type with at least an 60% accuracy. In the example, bone tags were identified with 93% accuracy, brain tags were identified with 92% accuracy, breast tags were identified with 85% accuracy, cecum tags were identified with 78% accuracy, colon tags were identified with 87% accuracy, heart tags were identified with 96% accuracy, intestine tags were identified with 77% accuracy, kidney tags were identified with 94% accuracy, liver tags were identified with 94% accuracy, lung tags were identified with 96% accuracy, pancreas tags were identified with 93% accuracy, prostate tags were identified with 88% accuracy, skin tags were identified with 93% accuracy, skin dorsal tags were identified with 60% accuracy, skin ventral tags were identified with 89% accuracy, and spleen tags were identified with 95% accuracy.

Figure 8:
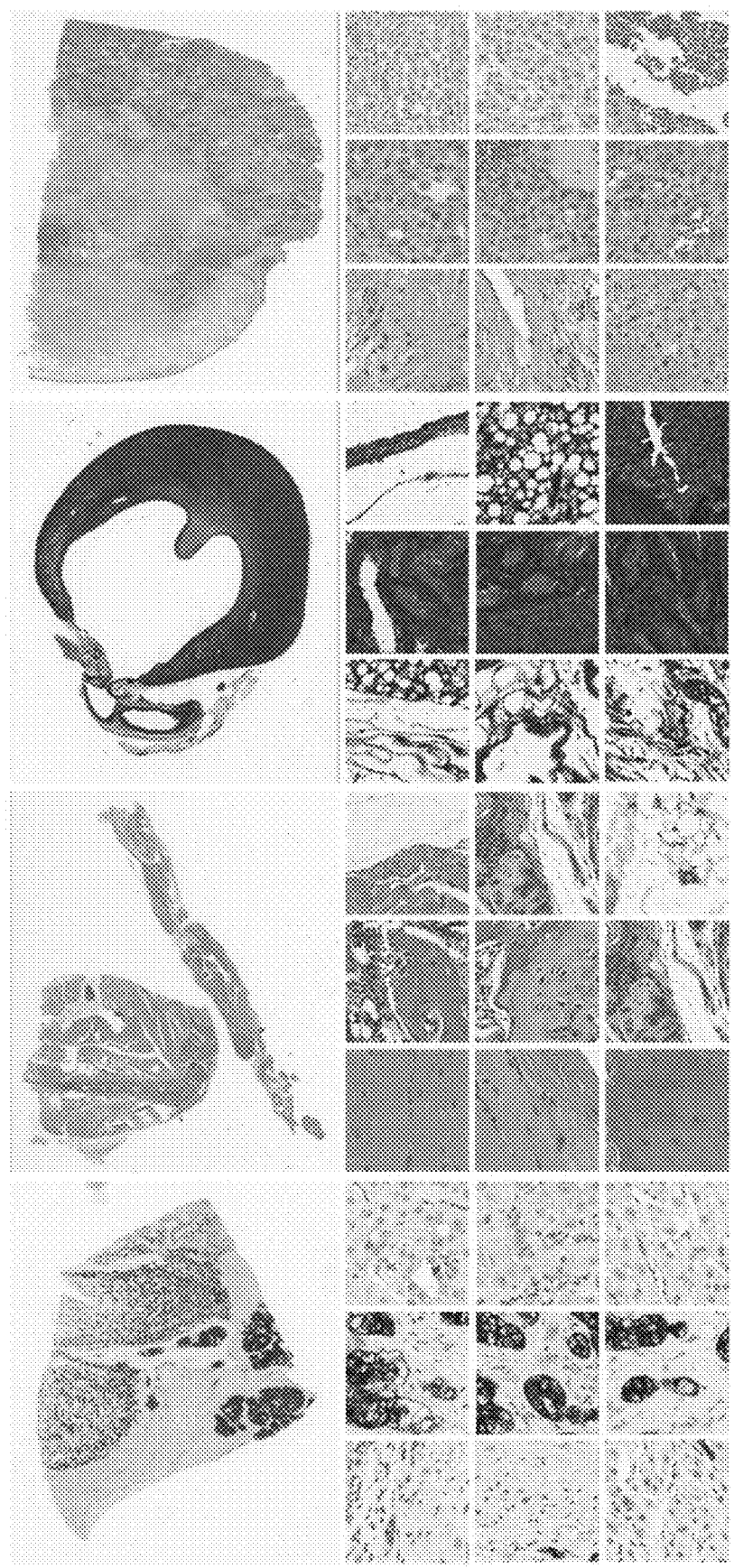
FIG. 8 depicts a non-limiting example of histology slides which have been analyzed using systems and methods disclosed herein.

In some embodiments, to visually validate the effect of multi-tag attention module, the attention weights as well as their corresponding patch images are collected and examined. FIG. 8 depicts four groups of examples. As depicted, each attention head focuses on different patch patterns. For instance, the attention head that aims at tagging stain labels may have a higher interest on patches with simpler textures but larger tissue areas. These patches may mainly contain apparent color patterns such as the blue dots for IHC, red and pink regions for H&E. In some embodiments, while for the species and organ attention heads, patches with relatively complex structures and textures are assigned higher attention weights as they provide more contextual information for tagging species and organ labels.

FIG. 8 depicts the multi-Tag Attention Module's attention result visualization, according to an example. In example, each WSI has three columns. Each of the three columns belongs to one of the three tags: Stain, Species, and Organ from left to right. In some embodiments, patches in the columns are sorted by attention weights in the corresponding tag from the top to the bottom. In some embodiments, the ground truth tags for the four WSIs are respectively: (IHC, Human, Liver), (H&E, Mouse, Bone), (Special Stain, Rat, Kidney), and (H&E, Mouse, Liver).

While preferred embodiments of the present subject matter have been shown and described herein, it will be obvious to those skilled in the art that such embodiments are provided by way of example only. Numerous variations, changes, and substitutions will now occur to those skilled in the art without departing from the subject matter described herein. It should be understood that various alternatives to the embodiments of the subject matter described herein may be employed in practice. It is intended that the following claims define the scope of the present subject matter and that methods and structures within the scope of these claims and their equivalents be covered thereby.

What is claimed is:

1. A method of automatic multi-tagging of whole slide histopathology images comprising:
   a) receiving a digital whole slide image;
   b) sampling a plurality of non-background patches from the whole slide image at a plurality of magnifications;
   c) applying a machine learning model to predict multiple slide-level tags from the plurality of non-background patches, wherein the machine learning model comprises:
      i. a first module configured to extract a visual feature representation of each patch;
      ii. a second module configured to modulate patch features by providing the extracted visual feature representations as inputs to a first attention aggregation mechanism performing operations comprising: mapping each visual feature representation into different attention-weighted features through multi-head attentions and outputting a weighted patch feature comprising an aggregation of the visual feature representations and the attention-weighted features;
         wherein the machine learning model operates in a multi-scale mode utilizing the patches at the plurality of magnifications to identify both patch features and magnification levels most discriminant for the multi-tagging;
      iii. a third module configured to construct slide-level tags identifying tag classifications by providing the weighted patch features to a plurality of second attention aggregation mechanisms, one per output head, each performing operations comprising: mapping each weighted patch feature into different attention-weighted features through multi-head attentions, and outputting a slide-level tag comprising an aggregation of the attention-weighted features; and
   d) associating the multiple slide-level tags with the digital whole slide image.

2. The method of claim 1, further comprising detecting regions of the slide comprising tissue, detecting regions of the slide comprising background, or both.

3. The method of claim 1, wherein the first module utilizes a neural network.

4. The method of claim 3, wherein the neural network is a deep neural network.

5. The method of claim 4, wherein the deep neural network comprises a ResNet architecture.

6. The method of claim 5, wherein the ResNet architecture comprises ResNet-34, ResNet-50, or ResNet-101.

7. The method of claim 1, wherein the second module utilizes a neural network.

8. The method of claim 7, wherein the neural network is a deep neural network.

9. The method of claim 1, wherein the first attention aggregation mechanism further performs operations comprising: adding a residual connection from each input to the output and directly aggregating it with each patch's weighted representations.

10. The method of claim 1, wherein the plurality of magnifications includes magnifications from about 4× to about 100×.

11. The method of claim 1, wherein the plurality of magnifications comprises about 3 magnifications to about 10 magnifications.

12. The method of claim 1, wherein the tags are selected from the group consisting of: species, age, gender, organ type, stain type, lesion type, cell type, disease type, antibodies, fixative type, gene expression, tumor type, biosystem, mouse strain, genetically engineered mouse model (GEMM), experiment, xenograft, promoter, reporter, and combinations thereof.

13. The method of claim 12, wherein lesion type comprises one or more of: tumor, necrosis, fibrosis, and metastasis.

14. The method of claim 12, wherein one or more of the tags are Boolean.

15. The method of claim 12, wherein one or more of the tags comprise a string defining a type.

16. The method of claim 12, wherein one or more of the tags comprise a string defining a severity.

17. The method of claim 12, wherein one or more of the tags comprise a string defining a location.

18. The method of claim 1, wherein each tag is associated with the digital whole slide image as a metadata field.

19. The method of claim 1, further comprising archiving the digital whole slide image and the associated tags in database.

20. The method of claim 19, further comprising providing a slide image search interface providing access to configure a slide image search module.

21. The method of claim 20, wherein the slide image search interface allows a user to perform a reverse image search.

22. The method of claim 20, wherein the slide image search interface allows a user to identify archived whole slide images by matching one or more tag attributes.

23. The method of claim 20, wherein the slide image search interface allows a user to identify archived whole slide images by thresholding one or more tag attributes.

24. The method of claim 1, wherein the machine learning model is trained under a multi-task learning scheme where each classification task is a multi-class classification problem.

25. A system comprising: at least one processor, a memory, and instructions executable by the at least one processor to create a whole slide histopathology image multi-tagging application comprising:
 a) a software module configured to receive a digital whole slide image and sample a plurality of non-background patches from the whole slide image at a plurality of magnifications;
 b) a machine learning model to predict multiple slide-level tags from the plurality of non-background patches, wherein the machine learning model comprises:
  i. a visual feature extraction module configured to extract a visual feature representation of each patch;
  ii. a patch transformation module configured to modulate patch features by providing the extracted visual feature representations as inputs to a first attention aggregation mechanism performing operations comprising: mapping each visual feature representation into different attention-weighted features through multi-head attentions and outputting a weighted patch feature comprising an aggregation of the visual feature representations and the attention-weighted features;
   wherein the machine learning model operates in a multi-scale mode utilizing the patches at the plurality of magnifications to identify both patch features and magnification levels most discriminant for the multi-tagging;
  iii. a multi-tag attention module configured to construct slide-level tags identifying tag classifications by providing the weighted patch features to a plurality of second attention aggregation mechanisms, one per output head, each performing operations comprising: mapping each weighted patch feature into different attention-weighted features through multi-head attentions, and outputting a slide-level tag comprising an aggregation of the attention-weighted features; and
 c) a software module configured to associate the multiple slide-level tags with the digital whole slide image.

26. A non-transitory computer-readable storage media encoded with a computer program including instructions executable by a processor to create a whole slide histopathology image multi-tagging application comprising:
 a) an intake module configured to receive a digital whole slide image and sample a plurality of non-background patches from the whole slide image at a plurality of magnifications;
 b) a machine learning model to predict multiple slide-level tags from the plurality of non-background patches, wherein the machine learning model comprises:
  i. a visual feature extraction module configured to extract a visual feature representation of each patch;
  ii. a patch transformation module configured to modulate patch features by providing the extracted visual feature representations as inputs to a first attention aggregation mechanism performing operations comprising: mapping each visual feature representation into different attention-weighted features through multi-head attentions and outputting a weighted patch feature comprising an aggregation of the visual feature representations and the attention-weighted features;
   wherein the machine learning model operates in a multi-scale mode utilizing the patches at the plurality of magnifications to identify both patch features and magnification levels most discriminant for the multi-tagging;
  iii. a multi-tag attention module configured to construct slide-level tags identifying tag classifications by providing the weighted patch features to a plurality of second attention aggregation mechanisms, one per output head, each performing operations comprising: mapping each weighted patch feature into different attention-weighted features through multi-head attentions, and outputting a slide-level tag comprising an aggregation of the attention-weighted features; and
 c) a tagging module configured to associate the multiple slide-level tags with the digital whole slide image.

* * * * *